United States Patent [19]

Reinhold, Jr. et al.

[11] Patent Number: 4,531,527

[45] Date of Patent: Jul. 30, 1985

[54] AMBULATORY MONITORING SYSTEM WITH REAL TIME ANALYSIS AND TELEPHONE TRANSMISSION

[75] Inventors: Herbert E. Reinhold, Jr., Rockville, Md.; Albert A. Auerbach, New York, N.Y.

[73] Assignee: Survival Technology, Inc., Bethesda, Md.

[21] Appl. No.: 403,775

[22] PCT Filed: Apr. 23, 1982

[86] PCT No.: PCT/US82/00525

§ 371 Date: Jul. 9, 1982

§ 102(e) Date: Jul. 9, 1982

[87] PCT Pub. No.: WO83/03744

PCT Pub. Date: Nov. 10, 1983

[51] Int. Cl.³ .............................................. A61B 5/04
[52] U.S. Cl. ..................................... 128/696; 128/903
[58] Field of Search ............... 128/419 PG, 696, 697, 128/709, 710, 711, 712, 904, 903

[56] References Cited

U.S. PATENT DOCUMENTS

| | | | |
|---|---|---|---|
| 3,199,508 | 8/1965 | Roth | 128/904 |
| 3,603,881 | 9/1971 | Thornton | 128/903 |
| 3,782,367 | 1/1974 | Hochberg et al. | 128/697 |
| 4,083,366 | 4/1978 | Gombrich et al. | 128/706 |
| 4,197,830 | 4/1980 | Schulman et al. | 128/419 PG |
| 4,250,888 | 2/1981 | Grosskopf | 128/702 |

OTHER PUBLICATIONS

Schmitt et al., "Journal of Clinical Engineering", Jan.–Mar. 1979, vol. 4, #1, pp. 49–53.

Primary Examiner—William E. Kamm
Attorney, Agent, or Firm—Cushman, Darby & Cushman

[57] ABSTRACT

A cardiac monitoring system for monitoring a plurality of patients including a plurality of patient-worn units and one or more office units. A patient unit detects a patient's EKG and analyzes the EKG in real time (during the patient's R-R interval). It provides morphology analysis, heart rate data, ST segment analysis, symptomatic and asymptomatic event recordings, and the counting of ectopic runs. The analyzed data is sent over a standard voice-grade telephone line or other suitable communication channel to an office which prepares a patient report for a physician. In addition, the office unit provides an interactive scheme by which various alarm and recording criteria are established for a particular patient at the time of hook-up. Also, the office unit automatically communicates with the physician under predetermined emergency circumstances so that a patient can get medical attention with a minimun time delay.

61 Claims, 13 Drawing Figures

| FAMILY | CHANNEL A | CHANNEL B | CHANNEL C | NO. OF BEATS | ESTIMATED % OF BEATS |
|---|---|---|---|---|---|
| I DOMINANT MORPHOLOGY | | | | 122,143 | 97.9 |
| II | | | | 2450 | 2. |
| III | | | | — | — |
| UP TO 8 FAMILIES | | | | | |
| | TOTAL NUMBER BEATS ANALYZED | | | 124,683 | 99.9 |

AMBULATORY MONITORING SYSTEM WITH REAL TIME ANALYSIS AND TELEPHONE TRANSMISSION

This invention relates to systems for acquiring and processing electrocardiographic (EKG) data.

BACKGROUND OF THE INVENTION

There are many medical situations presented where it is highly desirable, if not absolutely essential, for the attending physician to have data as to the patient's electrical heartbeat activity in order to make a sound medical judgment. The usual situation is one where the symptoms of a patient do not warrant hospitalization and yet require the generation of electrical heart activity data upon which the physician can make a sound medical judgment. Of course, where the patient is in a coronary care unit expensive and complex equipment can be provided to supply any and all required data. There are, however, additional hospital related situations where such data is useful and necessary as, for example, when the patient is beginning to move out of the coronary care unit within the hospital and then out of the hospital as an out-patient. In order to supply the required data in these situations beyond intensive coronary care, so-called "Holter" ambulatory monitors have been developed (e.g. U.S. Pat. No. 4,211,238). Originally devices of this type provided the simple capacity of recording in real time the electrical heart activity of a patient carrying or wearing the device for a 24 hour period.

The usual situation was for a physician to order the so-called Holter test requiring the patient to come into a facility where the operation of the device could be demonstrated and an initial connection to the patient could be affected. In conjunction with the operation of the device the patient was given a diary within which to record on a time basis activities during the 24 hour monitoring period as well as any symptomatic events which may occur. Many of the devices were provided with means by which the symptomatic events could be signaled in the tape by the patient pressing a button or the like. The usual procedure after monitoring had been completed required the patient then to come back to the facility and to disconnect the monitor so that the recorded data could then be processed for use by the attending physician.

Clearly it is impractical for a physician to have to spend 24 hours playing back the tape in order to assimilate the data represented by the same. Consequently, machines were developed for analyzing the tapes. The machines developed for this purpose (e.g. U.S. Pat. No. 4,073,011) all required manual operators who, by visual inspection of an oscilloscope or equivalent, made judgments such as abnormal cardiac activity as to which portions of the recording should be printed out as rhythm strips. Because of the operator judgment factor, the usual situation was to centralize the location of the processing machines so that skilled operators could be efficiently employed on a continuous basis. Consequently, while the practice of some doctors may be sufficiently specialized as to provide a volume sufficient to justify a full-time operator, the more prevalent method of operating was to centralize the operation to a point requiring that the recorded data be sent from the location where the monitor was connected and disconnected to a remote location which in many instances could be from a doctors office to a larger facility in a hospital or big city. Other alternatives included the setting aside of facilities in a hospital to perform both the connection and disconnection procedures as well as the data processing procedures.

In any event, in order to facilitate the data processing, the machines involved were developed so as to enable the tapes to be operated at ever increasing speeds. In the early machines speeds of the order of 60 times real time were utilized, whereas the more sophisticated and modern machines have operated at speeds of up to 480 times real time. It is generally accepted, however, that as speeds increased accuracy and/or consistency tended to decrease.

In order to recapture the lost accuracy of high speed processing, the monitors of more recent vintage have embodied therein the capability of analyzing the electrical EKG captured on a real time basis as it is being captured. (See, for example a paper entitled "Real Time Analysis of Holter ECG Data Represents a Major Technological Advance" by Norman H. Holter published in the Holter Research Foundation, Inc.) Further, these monitors were provided with the capability of selectively recording rhythm strips based upon the analyzation or real time processing being carried out. The use of these processing monitors seemed to offer a simplification of the subsequent processing required. However, the normal operating mode remained unchanged and there was subsequent processing required which, as before, was carried out at central locations with the attendant patient inconvenience and delays occasioned as a result of transportation time and scheduling of machine time.

While these recently proposed real time processing ambulatory monitors appear to offer the prospect of recapturing the lost accuracy associated with high speed machine processing and reducing to some extent the processing delays heretofore experienced, there still exists the need to further reduce these delays and to alleviate the patient inconveniences associated therewith.

SUMMARY OF THE INVENTION

Accordingly, it is an object of the present invention to provide an ambulatory monitoring system which will achieve all of the advantages of the real time processing heretofore obtained while at the same time fulfill the above identified need of further reducing the processing delays and alleviating the patient inconvenience associated therewith. In accordance with the principles of the present invention, this objective is obtained by providing a system which includes a multiplicity of individual ambulatory patient monitoring units each of which includes components provided for the purpose of achieving real time data processing and further providing the capability of transmitting the processed data over a communication channel (e.g. telephone) to a receiving office unit forming a part of the system which is capable of receiving the processed data and converting it into a form (patient report) suitable to the attending physician.

The capability of transmitting over a communication channel the processed data stored in the ambulatory unit after the monitoring period has been completed clearly constitutes a patient convenience and time saver as compared with the usual practice requiring that the unit containing the processed data be physically transported to the central location. Of greater significance perhaps is the versatility imparted to the system by the establishment of communication channel interaction between the office unit at the central location and the multiplicity of ambulatory units being operated by the patients. Basically, this communication channel interaction frees the ambulatory monitoring units from the restraints of a fundamental operating mode which consists of (1) hooking up the monitor to the patient, (2) monitoring for a predetermined period and (3) unhooking the monitor from the patient.

While this mode of operation often results in the production of data which is later determined to be sufficient for purposes of rendering a sound medical judgment, there are many occassions when the data produced is later found to be insufficient. Under these circumstances, the physician may order the patient to undergo another predetermined period of operating mode use of the monitor. With the convenience and time saving provided by the communication channel interaction of the present system the period of monitoring need not be regarded, as rigidly set. Instead, a more convenient earlier telephone transmittal of the processed data may be undertaken as a result of which the physician can almost immediately interact with the patient by virtue of the interacting of the units over the communication channel. In this way, a much longer rigidly set period of monitoring can be avoided where the physician is satisfied with the sufficiency of the processed data already received. Moreover, where the information received indicates the need for further information, a continued contiguous period of monitoring can be prescribed. This versatility is particularly advantageous in situations where the monitoring of the patient is being undertaken in conjunction with a program of medicament administration because it enables the physician to quickly and easily evaluate the patients progress at relatively short intervals under circumstances where the medication dosage can be immediately modified as indicated.

The capability of communication channel interaction between ambulatory monitoring units and a centrally located office unit not only provides the capability of transmitting processed data from the monitoring unit to the office unit but of transmitting information from the office unit to the monitor unit which will change its mode of processing the data in a continued contiguous monitoring period. This capability is particularly desirable in situations where the initial evaluation of the processed data indicates to the physician that it is insufficient and further information is required on a basis different from that originally contemplated. For example, in accordance with the principles of the present invention means is provided which is operable during the communication channel interacton to actually change the criteria stored within the monitoring unit for determining when a rhythm strip should be recorded. Alternatively, the processing basis itself can be changed. Patient notification, as by a buzzing and/or a LCD readout indicating a message such as "call office unit", becomes more meaningful in the light of the capability of being able to supply the physician with the processed data recorded for his immediate evaluation. While emergency situations are hopefully not presented with any frequency, nevertheless, there is always a danger of this type presented and the capability of immediate telephone availability of all processed data may prove to be life saving.

In addition to rapid telephone interaction between patient and physician in situations where the monitor has operated to notify the patient, a more rapid physician involvement becomes possible in situations where the readout of the processed data by the office unit indicates the desirability of immediate physician involvement, which involvement can be secured through a second communication channel.

The provision of a system which frees up the use of the monitoring unit from the somewhat rigid operating mode of (1) hook-up the monitor (2) monitor a predetermined period (3) unhook the monitor, makes possible the extended use of the monitor by a single patient or, alternatively, the permanent ownership of a unit by a patient in which case it is important that the communication channel interaction contemplate the transmittal of information as to the condition of the batteries powering the ambulatory unit. In accordance with the principles of the present invention such means is provided together with means for preventing the information stored in memory from being lost due to battery failure.

In accordance with the principles of the present invention the advantages described above can be obtained in a system in which the transmitting capability is provided in a separate modem. However, it is preferable to build into the ambulatory monitor itself the transmitting capability so that the monitor is self-contained, thus effecting further reduction in patient inconvenience and delay.

Accordingly it is a further object of the present invention to provide an ambulatory patient monitor unit for use in a system of the type described which includes means operatively connectable with a patient's body for providing an EKG signal indicative of electrical activity associated with a patient's heart action, means for sampling the EKG signal provided by said EKG signal providing means to provide a plurality of EKG signal samples, signal processing means for analyzing the EKG signal samples provided by said sampling means in real time and according to predetermined criteria and generating, as a result of that analysis, processed data to produce a corresponding patient report intelligible to a person skilled in coronary care, memory means for storing the processed data generated by the signal processing means, patient actuable transmitting means for causing the processed data stored in the memory means to be read from the memory means and to be transmitted over a communication channel, and portable housing means, suitable for being worn or carried by the patient, containing the sampling means, signal processing means, memory means, and transmitting means.

The term "sampling means" as set forth above contemplates both digital and analog sampling. That is, sampling of time increments at rates sufficient to provide a digital definitiion of the electrical activity associated with a single heartbeat or sampling of time increments at rates which would include all of the electrical activity associated with a single heartbeat.

Another object of the present invention is the provision of an ambulatory patient monitoring unit of the data processing type having means incorporated therein for transtelephonically initially storing and/or changing any one or any combination of the following criteria: (1) stored analysis criteria (2) rhythm strip recording criteria and (3) patient notification criteria.

It is recognized that there have been proposed ambulatory monitors having the capability of transmitting data over the telephone. One such proposed device is disclosed in articles entitled "An Intelligent Monitor for Ambulatory ECGS" by John G. Webster and "A Portable Microcomputer-Based System for Biomedical Applications" by Willis J. Tompkins, both published in Biomedical Sciences Instrumentation, Volume 14 (1978). The type of analysis carried out in real time by this proposed device is set forth in articles entitled "Reliable R-Wave Detection from Ambulatory Subjects" by Nitish V. Thaker and "Algorithms for Real-Time Ambulatory ECG Monitoring" by John P. Abenstein and "Arrhythmia Detection Program for an Ambulatory ECG Monitor" by William C. Mueller, all three articles being published in Biomedical Sciences Instrumentation, Volume 14 (1978).

The proposed device is not an ambulatory device for continuously monitoring over a predetermined period of time. Rather, it is an event recorder for capturing and recording a single 16 second event only. In this sense, it is an intermittent monitor. The proposed device measures the heartbeat waveforms against predetermined arrhythmia criteria. When any of the criteria are met, the device records 16-seconds of cardiac activity (a single 16-second rhythm strip) and alerts the patient that a recording has been made. The monitoring process then stops. The patient calls the physician's office over the telephone when this can be conveniently accomplished and plays back the 16-seconds rhythm strip to a central computer which causes the rhythm strip to be printed or otherwise displayed for the cardiologist.

The use of single event recorders such as the proposed one have not proved acceptable for monitoring a wide range of cardiac patients because only limited information is available, monitoring is not continuous and there is a high degree of patient inconvenience associated with placing a call to the central computer each time single 16-second event recordation is triggered.

Perhaps because of this increase in patient inconvenience, trans-telephonic communication as provided in these event recorders has not been heretofore applied as aforesaid to Holter-type monitors that continuously analyze EKG data over a predetermined period of time as a means to reduce the patient inconvenience thereof.

It is a further object of the present invention to provide an ambulatory patient unit which includes means operatively connectable with a patient's body for providing three EKG signals indicative of electrical activity associated with a patient's heart action, means for sampling each of the three EKG signals provided by the EKG signal providing means to provide a plurality of EKG signal samples, signal processing means for substantially simultaneously analyzing the samples of each of the three EKG signals provided by the sampling means in real time and according to predetermined criteria so as to obtain enhanced P-wave analysis and generating, as a result of that analysis, processed data to produce a corresponding patient report intelligible to a person skilled in coronary care, memory means for storing the processed data generated by the signal processing means, and portable housing means, suitable for being worn or carried by the patient, containing said sampling means, signal processing means and memory means.

It is recognized that three channels of EKG information have been analyzed in connection with more conventional monitors. See for example the article entitled "Unsupervised Template Construction for QRS Classification in Holter Tape Analysis" by M. B. Tartakousky et al, published in Computers in Cardiology, 1980. Three channels of EKG signals were fully recorded using a conventional Holter-type 24-hour tape monitor. These three channels were later computer analyzed. Despite the three channel work done with large computers, after the fact, on a pre-recorded tape, no one has successfully applied three channel real time analysis to an ambulatory monitoring device.

Another object of the present invention is the provision of a ambulatory patient unit which embodies means therein for transmitting processed data by telemetry so as to render the unit capable of use both inside and outside a hospital.

These and other objects of the present invention will become more apparent during the course of the following detailed description and appended claims.

The invention may best be understood with reference to the accompanying drawings wherein an illustrative embodiment is shown.

DETAILED DESCRIPTION OF THE PREFERRED EMBODIMENT SYSTEM OVERVIEW

Figure 1:
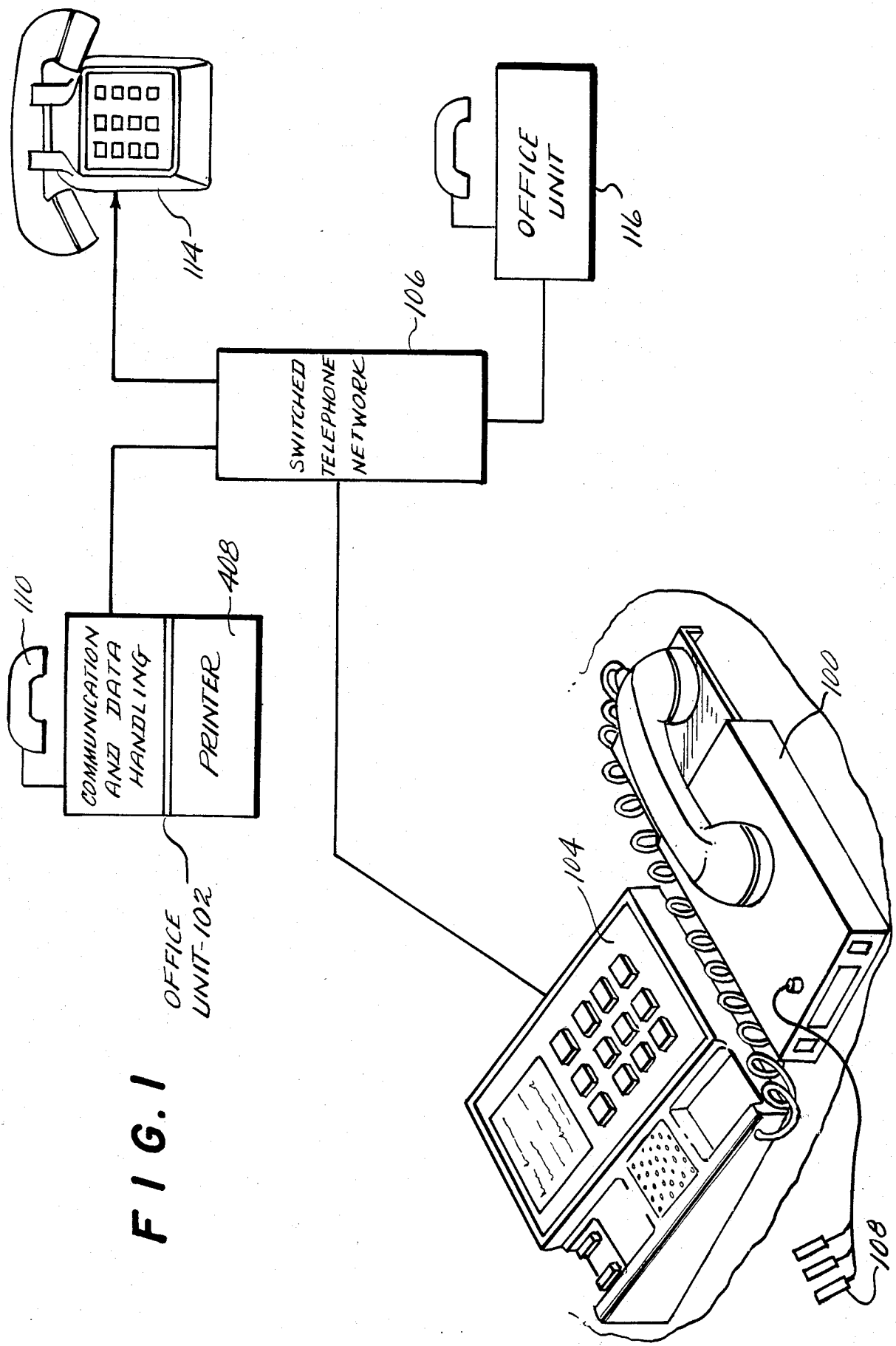
FIG. 1 is a general block diagram of the cardiac monitoring system according to the present invention.

Referring now to FIG. 1 there is shown a general block diagram of the cardiac monitoring system according to the present invention. The system is intended for use in cases where the physician wants to monitor a patient over an extended period of time such as 24, 48 or even 72 hours. The system comprises two primary components: a patient unit 100 that is portable and intended to be worn by an ambulatory heart patient and a physician's office unit 102.

Patient unit 100, during a test, collects electrocardiogram (EKG) data, analyzes it in real time according to predetermined analysis criteria, records cardiac events.

After the test or a portion of the test is complete, it transmits all of the information collected during the test or test portion over a communication channel, such as telephone system to office unit 102.

Office unit 102 is remotely located, usually at a physician's office, a hospital, or other cardiac monitoring facility and is capable of receiving information from a plurality of units 100. It includes a section for communicating with patient units or another office unit and a printer for preparing a hardcopy of a patient report. The telephone system is represented by a switched telephone network 106, a patient's telephone 104 and a physicians home telephone 114. Standard voice-grade telephone lines are assumed throughout.

Patient unit 100 includes an electrode system 108 having three (3) electrode pans for detecting the patient's EKG on three separate and distinct EKG channels. Patient unit 100 is an "intelligent" unit capable of analyzing under program control, in real time, and developing processed data indicative thereof. Patient unit 100 not only analyzes the patient's EKG data, but in addition, provides various notification alarm functions, and rhythm strip-type variable length cardiac event recordings. The criteria for the various alarms and recordings are preprogrammed into patient unit 100 at the time of patient hook-up. The criteria can be tailored to each patient.

The analysis performed includes a plurality of functions, all carried out in real time according to preprogrammed instructions in the patient unit. The patient's EKG signals on three (3) channels are sampled to isolate individual heartbeats and analyze it. Analysis of the sample is essentially on-going continuously with data being put into ques of varying priority.

The analysis program is organized as a real time process with interrupts so that the highest priority functions can be executed first. When a particular set of program steps is interrupted so that a high priority function, such as taking an EKG sample must occur, the abandoned program step is "pushed" into a program stock. When the high priority function is complete, the abandoned instruction "pops" out of the stack and execution of the program sequence continues where it left off. All information gathered during a test including processed data resulting from the real time analysis and any events recorded during the test is transmitted by acoustic coupling to the patient's telephone after the patient establishes communication with his physician's office unit 102 by dialing its dedicated telephone number.

Office unit 102, like patient unit 100, is a microprocessor-based device. Its general function is to receive information from patient unit 100 and to format and display this information in the form of a concise patient report for the physician. Office unit 102 is provided with a dedicated telephone number, symbolized by a handset 110. This dedicated phone number is given to each patient who is hooked up to a patient unit 100 so that the patient can dial the office unit from any location.

Office unit 102, in addition to formatting and displaying the patient report can carry out additional functions. Based on predetermined alert criteria for each patient, office unit 102 can, upon receipt of information from a patient unit, telephone directly to a physician or other coronary care personnel. For example, office unit 102, based on certain preprogrammed criteria might place a phone call to a physician's home telephone 114 if it receives information from a patient indicating that more than a predetermined number of ectopic runs occurred within a single hour of monitoring.

For the purpose of advising the physician by telephone, office unit 102 includes voice synthesis circuitry so that the unit can actually "talk" to the physician. The office unit is preprogrammed to synthesize a plurality of basic message formats. Each message format has one or more blanks for the insertion of particular data received from the patient unit. The specific patient data is inserted in the appropriate blank and the "spoken" message is given to the physician. The speech synthesizing circuitry includes the ability to sound out letters and numbers. In the presently preferred exemplary embodiment, when the office unit alerts the physician, it identifies the patient being reported by spelling out the patient's name, such as "J—O—E—S—M—I—T—H". Office unit 102 is also capable of communicating interactively with patient 100 over the telephone system so that the physician can trans-telephonically change various criteria on which the patient unit will operate. For example, the physician may wish to change the criteria for recording cardiac events or for sounding a patient alarm advising the patient to call for help. By providing a facility to change such criteria trans-telephonically, much time and energy is saved in making trips back and forth to the physician's office.

For example, a patient undergoing a 48 hour test could call in every 12 hours to dump his data. The physician could observe the events captured and elect to change the recording criteria for the next 12 hours. In addition, office unit 102 has the capability of communicating with identical office units such as office unit 116 via the telephone system. For example one physician may wish to transfer data to another physician or one office unit could poll another office unit to insure that it is operating to provide a "back-up". Or, one office unit could poll another office unit from a central location such as from a cardiac monitoring service like Medalert ®.

FUNCTIONAL DESCRIPTION OF PATIENT UNIT 100

Patient Unit Functional Overview

Patient unit 100 provides a plurality of patient monitoring functions. It analyzes the patient's EKG signals on up to three (3) distinct channels in real time (during the RR intervals between heartbeats) to provide analyzed or processed data summarizing the test. Based on predetermined and trans-telephonically changeable asymptomatic event recording criteria patient unit 100 can record (store) a plurality of variable length cardiac events in "rhythm strip" form. Events can also be recorded in response to patient activation of a "symptom" button when the patient experiences some symptom. The patient unit also includes multiple notification alarms for alerting the patient that predetermined alarm criteria have been met such as, for example, a heart rate exceeding a predetermined high rate limit.

The unit 100 includes, within its portable housing, means for communicating over a standard voice-grade telephone line with an office unit 102 at a remote location. Such communication is useful for dumping all of the data collected during the test and for interactively communicating with a physician's office unit so that event recording and alarm criteria can be changed trans-telephonically. It is contemplated that a patient unit will establish telephone communication with an office unit and dump its collected and analyzed data. The office unit receives the dumped data, error checks it and if it is apparently error free, acknowledges receipt of the data. The acknowledgment causes the patient unit to clear its memory of all data.

The total EKG signal analysis program including analog to digital (A/D) conversion of input EKG signals, data compression, noise elimination, computation, categorization and counting of heartbeat wave forms, storage and output control, etc., takes place in real time.

Figure 2:
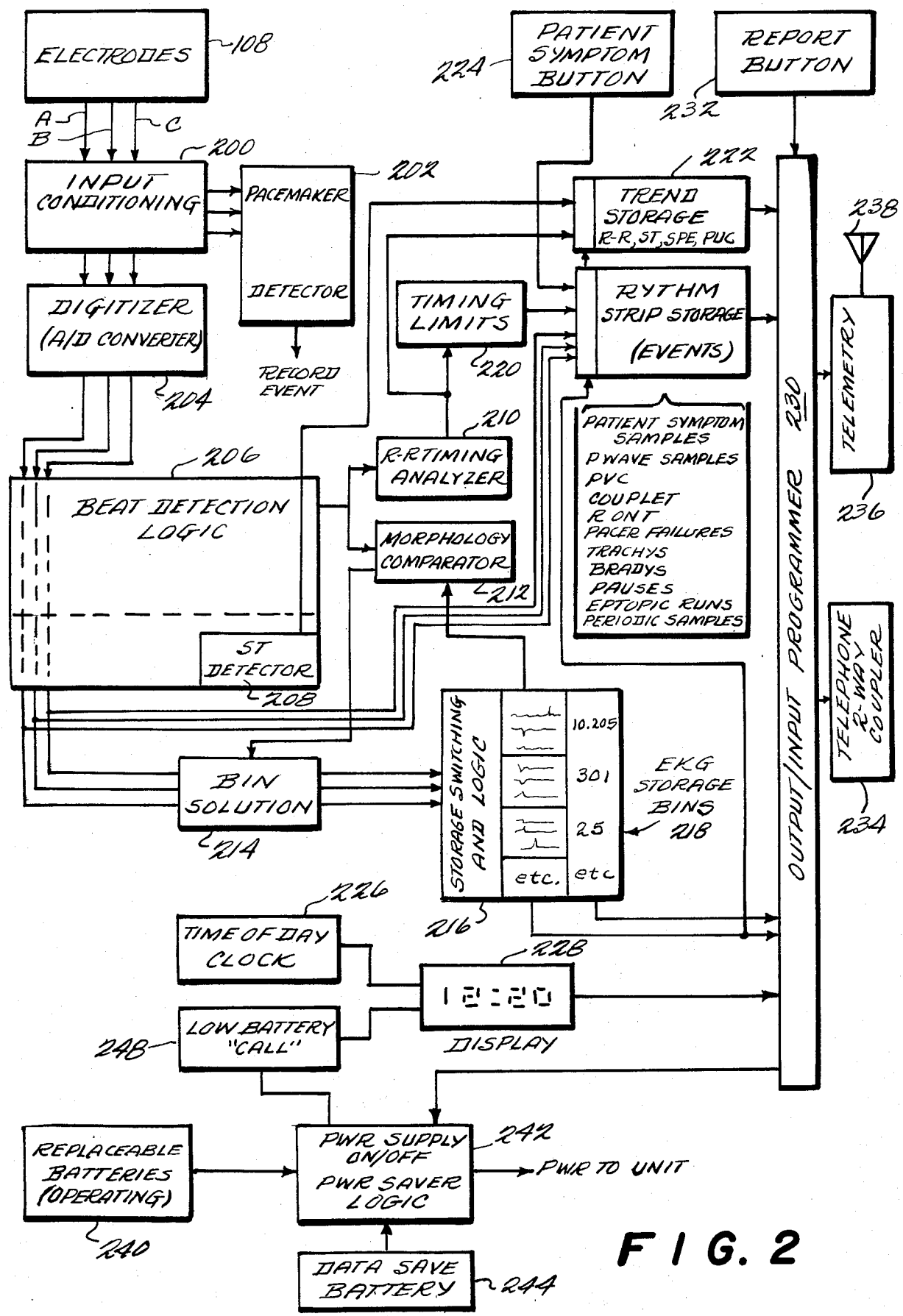
FIG. 2 is a functional block diagram of patient unit 100.

Referring now to FIG. 2 there is shown a functional block diagram illustrating the operation of patient unit 100. Many of the functional blocks represent functions carried out essentially by program instructions transforming the patient unit's microprocessor into a special purpose computer. Of course, it would be possible to carry out these functions with other types of circuits. However, for optimum performance, efficiency and size, the specially programmed microcomputer is the preferred structure implementation of these functions. Thus many of the functional blocks actually represent program blocks or groups of program instructions or steps rather than actual hardware.

Figure 12:
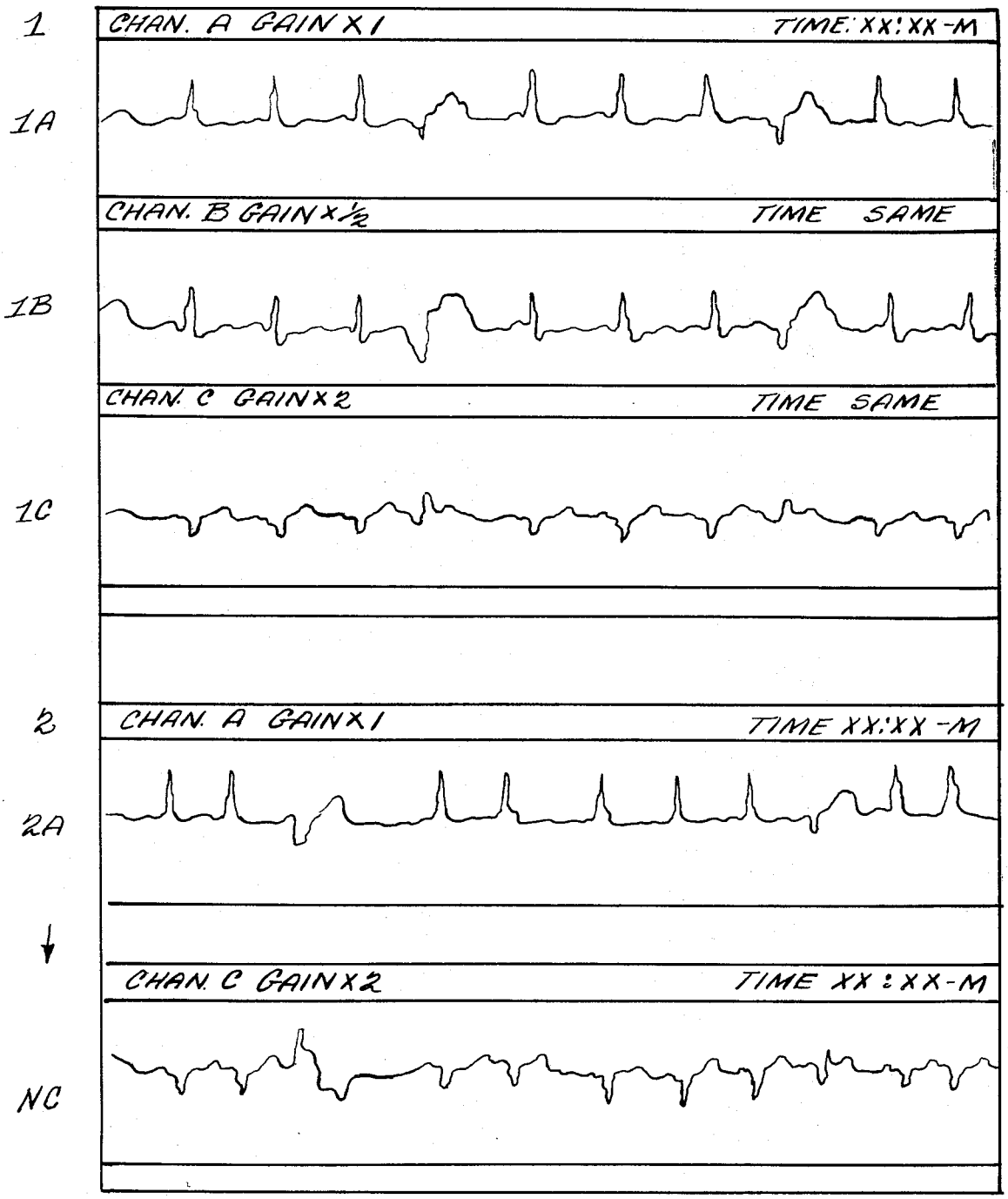
FIG. 12 is a diagram indicating the format for displaying pacemaker failures, symptomatic recordings, routine samples and criteria recordings from the patient report.

Electrodes 108, attached to the patient provide EKG signals on three (3) channels A, B and C. These EKG signals are conditioned by input conditioning circuitry 200. After the input signals are conditioned, they are coupled to both a pacemaker detector 202 and to a digitizer 204. Pacemaker detector 202 is specifically programmed to detect pacemaker malfunctions and to cause an event to be stored in memory 222. These recorded events are produced in the patient report under the heading "Pacemaker Failures" (See FIG. 12). Digitizer 204 (an analog to digital converter) digitizes the conditioned EKG signals on all three (3) channels at periodic intervals to provide digitized values suitable for analysis by computer. Of course, the digital conversion takes place at a high enough frequency according to sampling theory so that there is sufficient information available for characterizing the individual heartbeat waveforms.

The digitized values are coupled to beat detection logic 206 for detecting and isolating each heartbeat on each channels EKG signal. In essence, this provides a sampling of the EKG signals. Individual heartbeats are "extracted" from the stream of heartbeat waveforms that makeup the EKG signal on each channel. Beat detection logic 206 includes an ST segment detector 208 specifically for detecting the ST portion of each heartbeat waveform.

The individual heartbeat waveforms identified by beat detection logic 206 are coupled to an R—R timing analyzer 210 and to a morphology comparator 212, the operation of which will be further explained below.

Heartbeats of different morphology (shape) are recognized by patient unit 100 and a count of the number of each particular shape beat is accumulated. Heartbeats determined by beat detection logic 206 are coupled to a bin solution block 214 which provides individual heartbeat waveforms to storage switching and logic circuit 216 controlling the storage of the individual beat waveforms in EKG storage bins 218. Morphology comparator 212, bin solution 214, storage switching and logic 216 and EKG storage bins 218 together cooperate to analyze and store morphological data about the patient's heartbeat. In essence, each heartbeat is compared with heartbeats already stored as a template in EKG storage bins 218. If the heartbeat under consideration is sufficiently similar to one of the templates previously stored, the tally for the number of beats corresponding to the template is incremented by 1. The beat under consideration is compared with each template that is already stored in bins 218 to determine if there is a match with any of them. If the beat under consideration is sufficiently different from all of the templates previously stored, a new template is created to match the beat under consideration and appropriately stored in bins 218. This is done for each successive beat. In the presently preferred exemplary embodiment, up to eight (8) different heartbeat waveform templates can be stored in bins 218.

The output of R—R timing analyzer 210 is coupled to a timing limit slot 220 and to a memory 222 for storing symptomatic and asymptomatic cardiac events in rhythm strip form, processed data defining at least a portion of a patient report including trend data including R—R, ST, SPE and PVC histogram data. The patient report described later in this patent and shown in part in the drawings details the specific data accumulated in memory 222.

Patient unit 100 includes a patient symptom button 224 which can be patient actuated to cause an eight second rhythm strip to be stored in symptomatic memory. Typically, when a patient experiences a certain symptom, he will press button 224 to cause a recordation of an eight (8) second cardiac event. Data from bins 218 and memory 222 along with data indicative of the time at which various events or reduced data were accumulated indicating by a time of day clock 226 coupled through a display 228 are all coupled to an output-/input programmer 230 controlled by a report button 232. Display 228 is preferably a four (4) digit liquid crystal display. It not only displays the time of day from clock 226, but also serves various notification functions. For example, it can display a "CALL" message to the patient when the patient unit operating batteries begin to fail, as will be further discussed below. By actuating the report button 232, the patient can cause the data accumulated by programmer 230 to be transmitted via a telephone two-way coupler or by a telemetry circuit 236 to an antenna 238. In the presently preferred embodiment, antenna 238 is formed by one or more ground leads of the eletrode system. Patient unit 100 includes means for measuring the EKG signal samples against predetermined notification (alarm) criteria. If any notification conditions are met, a patient alarm (not shown) is activated. The alarm function can be enhanced by use of the internal telemetry. For example, patient units 100 could be used in a hospital to monitor a plurality of patients. Specific alarm criteria could be set for each patient. The alarm information could be transmitted via telemetry to a central monitor.

Patient unit 100 is powered by replaceable operating batteries 240. Power is applied to the various functional circuits through a power supply and power saver logic circuit 242. Patient unit 100 also includes data save battery 244 for supplying emergency power to the unit when replaceable operating batteries 240 become drained. When the replaceable batteries 240 become drained, the data save battery 244 is used to maintain the data previously analyzed and accumulated in memory 222. Power from data save battery 244 is not used for the accumulation of further data. A low battery call circuit 248 is provided for monitoring the condition of batteries 240 and 244. When a low battery condition is detected, circuit 248 generates a "CALL" signal that will replace the time of day signal normally displayed by display 228. This will alert the patient to call the physician's office or take other appropriate measures to dump his data to an office unit 102. A battery condition message can also be transmitted along with data from memory 222 when a patient dumps his data to office unit 102. The specific EKG signal analysis and event recording functions of patient unit 100 will now be described in further detail. In essence, what follows is a functional description of the program associated with patient unit 100 for executing its desired functions.

Morphological (Shape) Data

Figure 11:
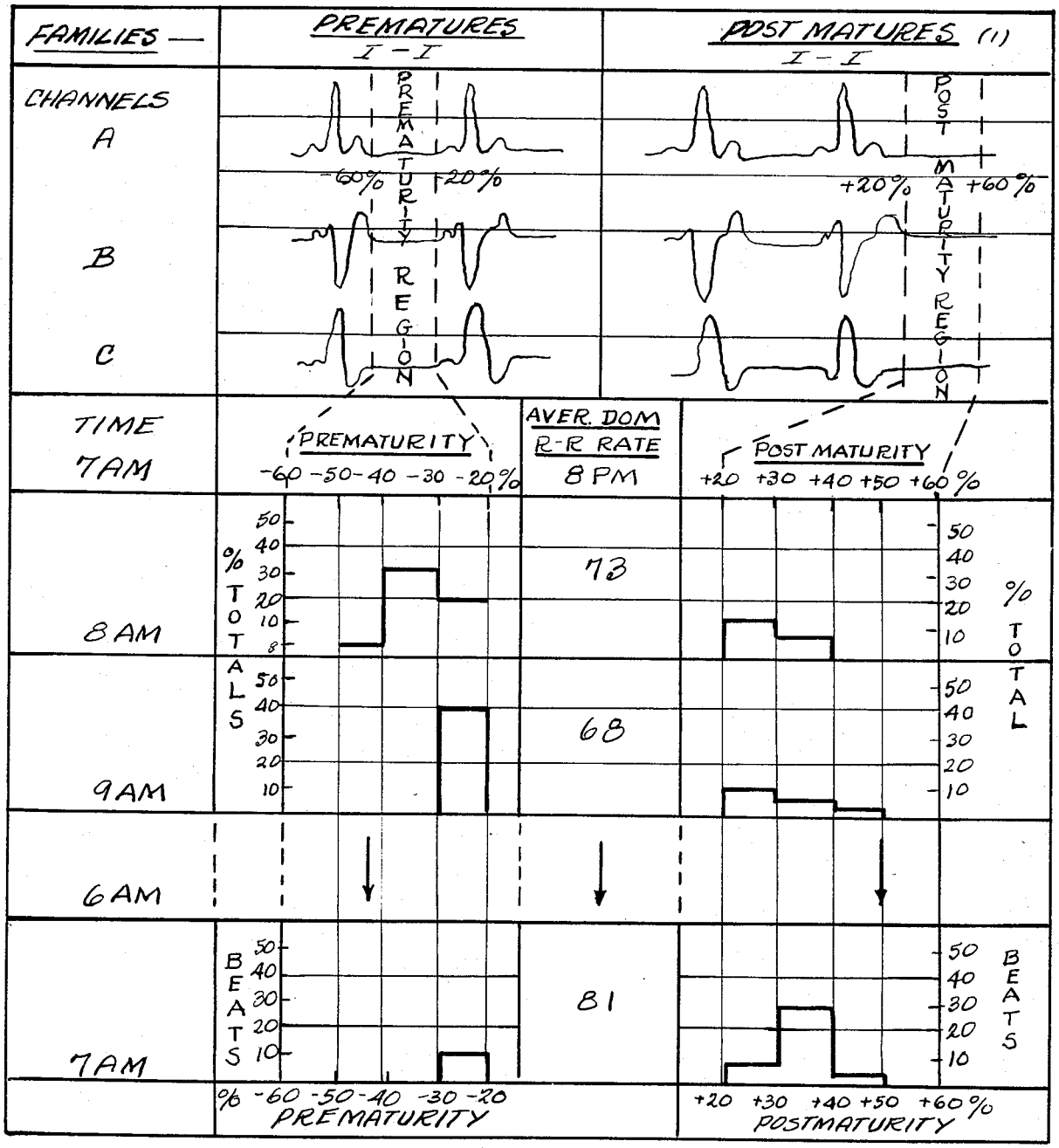
FIG. 11 is a diagram of prematurity and postmaturity symbolic data for illustrative purposes only from the patient report.

Heart beats of different morphology are recognized and counted. The patient report produced by office unit 102 distributes these counts into one hour periods (histogram). As shown the patient report set forth later in this description and shown in part in the drawings the distribution also recognizes the prematurity and lateness of each individual beat with respect to an "average" rate based on the last 16 beats of the dominant rhythm, i.e., the beats which show the highest number of counts. In the presently preferred format, there are eight prematurity and lateness groups as shown in FIG. 11. The number of such groups may, however in alternative embodiments of the invention, be increased or decreased according to the accuracy desired.

RR Rate Data

In addition to morphological analysis, the program analyzes heartbeat rate information, i.e. RR rate data. RR rates are distributed into ten (10) beats per minute intervals in a histogram and into twenty (20) beats per minute intervals in a table printed as part of the patient report. In the patient report set forth later in this description, additional distribution is shown which displays the minimum, average, and maximum rates in beats per minute within each one hour period.

ST Segment Analysis

Changes in the level of the ST segment, in millimeters of deflection with respect to an average (categorized) beat, are distributed on an hourly basis. The maximum and minimum values of the ST segment level, within each hour, are displayed or printed by office unit 102.

The measurement of ST segment amplitude requires that an EKG amplifier within patient unit 100 be calibrated with respect to a standard 1 millivolt test signal and that it hold this calibration to within about 5% over a 24 hr. period (i.e., the duration of a standard test). The stability of the calibration is indicated by a fixed deflection, of a printer associated with office unit 102, of one centimeter per millivolt (peak to peak) of EKG input signal. (Depending on use, by the physician, of other programmed amplifier gain settings, (x2 or x1/2), the deflections could also be 2 centimeters or ½ centimeter per millivolt (pp) respectively.) These calibrations are to be visualized by appropriate square waves (e.g.-three cycles at 5 Hz) at the beginning of the first rhythm strip (only) in the printed report.

Under the condition that printer is unavailable, one of the three gain settings above is chosen automatically so as to keep the signal within a permissible dynamic range. This is done during the patient "hookup" (later discussed). Once selected, the gain remains unchanged for the duration of the test.

Event Recordings

In addition to the analysis performed by the program, patient unit 100 is capable of recording a plurality of cardiac events in rhythm-strip format, each having a predetermined duration such as eight (8) seconds. These events are recorded as a sequence of digitized values in memory and are presented in each patient report prepared by office unit 102. The events may be either patient initiated (Symptomatic) recordings caused by the patient pressing symptom button 224 or automatically initiated (Asymptomatic) as a result of a positive comparison of EKG signal samples with predetermined asymptomatic event recording criteria. The recorded event in either case, starts a predetermined time before, and ends a predetermined time after, the condition which initiated the recording.

A symptomatic event is initiated by the patient whenever the patient pushes SYMPTOM button 224. Only a first predetermined number pushes of this button will produce an event recording of a standard length such as 8 seconds. The maximum number of events to be recorded is specified by the physican at the time the patient is "hooked-up". All subsequent pushes of SYMPTOM button 224 are counted and included as part of the report, together with the times at which the button was pushed even though the actual event is not recorded. This tells the physician when the patient experienced symptoms.

Asymptomatic Events

An asymptomatic recording is defined as an EKG record which: (a) meets certain numerical criteria relating to preset limiting values of the beat to beat intervals, i.e. is outside of certain specified high or low limits; or (b) meets certain criteria with regard to the number of consecutive beats in a sequence of ectopic beats; or (c) shows the first occurrence of a new (morphologically different) beat; or (d) exceeds a selected numerical criteria on permissible ST segment variation. In cases (a) and (b) and (c), the recording again brackets a time frame a predetermined number of seconds before and a predetermined number of seconds after the time that these criteria are met. In case (d), one frame of a current "ten beat average" beat of the dominant rhythm is recorded.

The asymptomatic event recording criteria data, for each test, can be programmed into patient unit 100, by the physician, during patient hook-up. If such action is not taken, certain "default definitions" or standard limits, automatically control the conditions for asymptomatic recording.

As each event is recorded, certain coded data which characterize the event are generated and are "attached" to the EKG recorded event. This data is used: (a) to assure that the number of recorded asymptomatic events of a given class is limited to a predefined number of recordings; and (b) to count events in each class, record each time of occurrence, and display the total counts as part of a summary report. As each event is "printed" by terminal unit 34, appropriate descriptive headings, based on the code produced during the original recording, are printed together with the event, to indicate the basis for the recording.

Ectopic Runs

Patient unit 100 also notes ectopic runs. All N-plet sequences, i.e., doublets, triplets, quadruplets or higher number of consecutive beats which differ in morphology from the dominant rhythm, are counted. The counts are distributed into hourly periods. The format is illustrated in the patient report set forth later in this description.

Summary Data

One section of the patient report is reserved for summary data. Control and criteria settings, as described further below, are tabulated here, together with descriptive and numerical data on pacemaker failures, etc. Additional summary data may include symptomatic and asymptomatic event tabulations, in which the events are classified by rate, rhythm and morphology, as well as their time of occurrence and number of occurrences; alarm activations (if any) and when they occurred, etc, etc.

Overflow

If the total number of cardic events (either asymptomatic or symptomatic) exceeds a predetermined number specified by the physician during hook-up (see patient report) an OVERFLOW condition occurs. In this case, overflow data is categorized and counted and the various counts thereby generated are included in the summary section of the patient report.

EKG "samples" (events) of relatively short duration can be recorded at regular (relatively infrequent) intervals during the test period. The recording time and frequency are specified during the patient hookup.

The various categories of data are numerically distributed by time (into one hour intervals), as well as by frequency. At the physician's option, this data can also be restructured into a histogram and trend format at office unit 102. Instructions to print data in such formats can be entered by the physician during the patient hookup. (The procedures for entering such instructions are discussed later).

Input Channels

Patient unit 100 uses three EKG channels A, B and C, and is capable of analyzing the EKG signals on all three (3) channels substantially simultaneously. By analyzing on three (3) channels, the morphology of each beat can be more accurately determined. For example, P-waves are more easily extracted from a noisy background and P-wave analysis is therefore enhanced. In addition to analyzing on three (3) channels, the patient unit can record on up to three channels. At the time of patient hook-up, the physician can make a determination as to the number of channels he would like to have on each event to be recorded in memory. However, there is a finite amount of memory. If he wants views from all three channels (all three electrode pairs) for each event he will not be able to record as many events as he would be able to record with fewer views of each event. This tradeoff is a medical judgment based on the type of information sought by the physician for a particular test.

The stability of the input amplifiers of patient unit 100 is monitored by control circuits which establish a constant printer output of office unit 102 at a normal (unprogrammed) gain of 1 cm/mv of EKG input signal.

One of the EKG amplifiers has the ability to recognize pacemaker spikes and simultaneously generate a pulse which will be used to transfer the time of occurrence of the spike from the Microprocessor's "real time clock" 226 into an addressable memory. Having been recognized, the spike is arbitrarily recorded in memory as having a positive amplitude of 0.3 millivolts and a duration of 10 milliseconds.

Electrodes and Hook-up

The integrity of the total electrode system 108 is checked automatically by circuits within patient unit 100. If an intermittent or open circuit condition is detected, an identifying code for the specific "electrode pair" of electrode system 108 (see FIG. 1) which failed is recorded, together with the time at which this condition started and ended. This information is included as part of the summary section of the printed patient report prepared by office unit 102.

In general, electrodes are "hooked up" to the patient in the course of his visit to his physician's office. Patient unit 100 includes two types of outputs: an FM analog signal output and an FSK digital signal output. Either of these can be transmitted by telemetry or over the telephone. The physician may not have an office unit 102, in which case an FM demodulator is acoustically coupled to patient unit 100 and the output of this demodulator is coupled to the physician's EKG machine. The patient's EKG can thus be visualized and the integrity of the system can be concurrently checked.

If the physician does have an office unit 102, the patient's electrodes are somewhat more readily checked, since the EKG will appear on the screen of a CRT included as part of office unit 102. It is expected that the EKG will usually be derived by direct acoustic coupling to the office unit 102.

As stated above, it is possible for the patient to be hooked-up by telemetry technique available hook-up. This technique permits the patient greater freedom of movement during the hookup and electrode check. Patient unit 100 includes, for this purpose, telemetry circuitry 236 and an antenna 238 as shown in FIG. 2.

Electrode system 108 includes three electrode pairs and a common electrode for a total of seven (7) electrodes. These electrode pairs can be arranged on the patient at the discretion of the physician using his best medical adjustment. As an example, the physician may select to use the Frank input arrangement to produce a vector cardiogram or he may elect to use some other electrode arrangement. Electrode system 108, including the seven (7) leads is provided as a bundle with a breakout of individual leads approximately two feet from the point of electrode attachment to the patient.

Patient unit 100 uses its memory not only for storing processed data and cardiac events but also for storage of the various parameters used for EKG analysis. Storage of cardiac events alarm criteria, etc. These parameters include, for example high and low RR rate criteria; current pacemaker rate; various alarm limits such as the maximum permitted ST segment changes; sampling protocols (sample frequency and duration), etc. This data is inserted in digital form by means of standard acoustic coupling. If it is not inserted by the physician, standard pre-programmed "default" data is used. A complete listing of the types of data insertable at the time of patient hook-up can be found in the hook-up report set forth later in this description.

In alternative embodiments of the invention, electroencephalographic (EEG), blood pressure, respiratory rate, or other inputs are possible input options. It is assumed here such data will be entered into the patient unit 100 by means of an external (stand-alone) device whose outputs are taken to the same input plug used for the EKG electrode leads. Simultaneous processing of EKG and blood pressure data, for example, will thus make use of only the three existing EKG data channels. The additional input device will include at least one impedance bridge capable of measuring variations, in the 1000 ohm range, of about 2-3% with an accuracy of about 5%.

One possible (accidental) input to patient unit 100 could be the high electrical potentials generated by a defibrillator. Therefore, patient unit 100 may incorporate a protective circuit to prevent damage by such potentials.

Local Or Remote Operation

As previously noted, information produced by patient unit 100 can be communicated from the patient unit in two distinct ways. First, it can produce frequency modulated (FM) analog signal and secondly it can produce a frequency shift keyed (FSK) digital signal. Either the analog or digital signal can be transmitted by telephone using an acoustic transducer or by telemetry on an appropriate RF frequency.

This variety of information output allows patient unit 100 to be compatible both with its intended office unit 102 and with known commercially available equipment that may be found in the physician's office such as a standard office EKG machine with an appropriate demodulator interface or a Decodalyzer.

Digital Data Transfer

Digital data, such as the control data entered above, or the report data transmitted via telephone line, radio link, or other communication channel to office unit 102, is serialized and modulates a "carrier" signal so as to permit bilateral transtelephonic or "direct audio" communication between the patient unit and the terminal unit. This data is advantageously communicated in a half-duplex mode. Full-duplex communication between office unit 102 and patient unit 100, although possible, is not required. Standard telephone modem frequencies are used, as tabulated below:

| | | |
|---|---|---|
| 1270 Hz | Transmits: | Mark (logic 1) = |
| Office Unit 102 | | Space (logic 0) = |
| 1070 Hz | | |
| | Receives: | Mark.. = 2225 Hz |
| | | Space. = 2025 Hz |
| | Transmits: | Mark.. = 2225 Hz |
| Patient Unit 100 | | Space. = 2025 Hz |
| | Receives: | Mark.. = 1270 Hz |
| | | Space. = 1070 Hz |

Acoustic FM

Patient unit 100 includes an acoustic FM output for transmitting data in analog form to conventional and widely available compatible equipment. In this mode of operation, the three (3) EKG channels A, B and C are alternately transmitted in 10 second sequences by modulating a 1700 Hz carrier in the United States (a 1500 Hz carrier in Europe). For compatibility with existing Decodalyzers, a frequency deviation of ±127.5 Hz/mv from this carrier is used. Frequency limiters may be included to avoid long distance "disconnects".

Patient unit 100 also includes an acoustic digital frequency shift key (FSK) output. This audio output is turned on when the patient pushes REPORT button 232, as described below. In transmitting digital information, only "zero" (space) and "one" (mark) frequencies are required. The frequencies used are 1070 Hz and 1270 Hz respectively.

Notifications (Alarms)

Patient unit 100 includes the capability of sounding two different notification alarms or "chimes" which may be dinstinguished by their respective tone frequencies. These chimes may be sounded at fast or slow intervals to provide further distinction of alarm functions. It is presently contemplated that alarms be included in patient unit 100. However, a physician hooking up a patient may choose not to have the alarm sounded. The alarms are provided so that the physician may set predetermined alarm criteria at the time of patient hook-up. During analysis of the EKG signal samples, when alarm conditions are met appropriate notification information is generated. This information can be used to sound a patient alarm if the physician desires that an alarm be sounded. Otherwise, the alarm information can simply be stored in memory and transmitted with other data collected during the test. The specific alarm criteria are set forth in the hook-up report provided near the end of this description. Item 15 sets forth the notification (alarm) criteria. These criteria include rates, PVC's, ectopic runs and ST changes.

It is contemplated that various equipment malfunction alarms be included within patient unit 100. However equipment malfunctions are not intended to sound a patient alarm. Rather, they will only be noted and stored in memory for transmission to office unit 102 and possible inclusion in the patient report.

Visible Clock

A carrying case for patient unit 100 incorporates a conventional digital clock 226 (see FIG. 2) and display 228 which will be easily visible to the patient. Clock 226 may be used to correlate symptomatic events with entries by the patient into a patient diary. During the patient hookup, clock 226 should be set under program control to correspond to the actual time in the patient's specific time zone.

Variables

Control and selection data involved in the operation of patient unit 100 is inserted into patient unit 100 memory under program control at hook-up. This procedure is described below in connection with the data insertion "dialogue" between the physician and office unit. The parameters inserted at hook-up are listed in the hook-up report set forth later in this description. The following explanation details some of these criteria.

PAUSE: This is a two digit number which specifies a rate, between 40 and 80 beats per minute. Examination of this number controls the point at which an automatic recording is made when one (1) RR interval is greater than the selected limit. As noted above, predetermined number of seconds before and after this point in time are recorded. Insertion of this control number will also permit activation of the audible rate alarm.

LOW RATE RUN: This is a number between 40 and 80, which is inserted under program control. The selected number defines the point at which automatic recording is initiated when two (or more) successive RR intervals exceeds the selected limit. An audible alarm is permitted only if this number is inserted.

HIGH RATE RUN: This is a number specifying a limiting rate between 80 and 140 beats per minute. If two or more successive RR intervals are less than the selected limit, automatic recording is initiated. The recording is the standard eight (8) second recording interval. Insertion of this number permits an audible alarm.

PACEMAKER RATE: This rate is a two digit number set to the intrinsic pacemaker rate at the beginning of the test. When the pacemaker is continuously inhibited, this rate must be determined by a magnet test.

ST SEGMENT VARIATION LIMITS: These are two numbers (positive elevation and negative depression) which are inserted under program control, defining in millimeters the asymptomatic ST segment limits. When the ST threshold exceeds the selected limit, an automatic recording of the most recent "ten beat average" for the dominant rhythm is made. The insertion of an ST segment limit permits the activation of the ST audible alarm if the limit is exceeded.

MAX. NUMBER OF EVENT RECORDINGS: These are numbers, inserted under program control, which define the number of various kinds of events to be recorded and stored in memory. To avoid an OVERFLOW condition, these numbers must be specified by the physician so that the recordings occupy no more than some specified portion of the event memory of patient unit 100. These include pacemaker failures, ST changes, ecopic runs, tachyarrhythmias, brady arrhythmas and symtomatics. Some of these are explained below.

SYMPTOMATICS: This is control information which is inserted by the physician to define the maximum number of symptomatic recordings, which the patient will be permitted to make by pressing symptom button 224.

ECTOPIC RUNS: This is a 2 decimal digit number, which specifies a limiting value for the number of consecutive beats having a morphology which differs from that of the dominant rhythm. An asymptomatic recording is initiated if this limit is exceeded. Insertion of this number will permit the activation of an audible alarm.

MAXIMUM NUMBER OF TACHYARRHYTHMIC RECORDINGS: This is a two decimal digit number which specifies the maximum number of tachyarrhythmic event recordings permitted for storage into the patient unit's event memory. (This number is selected by the physician during patient hookup, with consideration of course being given to specific patient problems as well as the possibility of an OVERFLOW condition.) Tachyarrhythmic events can include ectopic runs, atrial and ventricular premature beats, paroxysmal rhythms, bigeminy and trigeminy, interpolated PVC's and R on T phenomena. Events in excess of the number specified are counted, defined and classified as specific subgroups (directly above) and tabulated as part of the summary data in the patient report prepared by the office unit.

MAXIMUM NUMBER OF BRADYARRYTHMIC RECORDINGS: This is a two digit number specified by the physician during the patient hookup as the limiting number of bradyarrhythmic events to be permitted into event storage. The OVERFLOW conditions above again apply. Bradyarrhythmic events can include skipped beats, asystole in excess of a specified period, e.g.-a PVC followed by a compensatory pause, bigeminy and trigeminy, etc. As above, events in excess of the number specified are counted, defined and classified, and tabulated as part of the Summary Data in the Patient Report.

IDENTIFICATION: During patient hook-up, certain critical header information is programmed into patient unit 100. This critical header information identifies the patient and various other critical data that will help to identify any patient report subsequently prepared by office unit 102. This critical header information is set forth on the first page of the hook-up report set forth in detail later in this description. In the preferred report as presently contemplated, the critical information includes a hook-up date, patient identification including name, address, phone number, age, sex, height, weight, hospital, physician's name and address, physician's office phone number, etc.

ALARM ACTIVATION: Each of the patient unit alarms must be specifically authorized by the physician during the patient hookup in order to be made audible. As described below, authorization is provided by appropriate menu selection using the office unit 102 keyboard and CRT during an interactive hook-up procedure. The specific conditions which can be enabled by the physician are listed in the hook-up report set forth near the end of this description.

In addition, it is possible during the same menu selection process for the physician to specify the use of an emergency alarm. The presumption here is that the patient has been instructed by the physician to call his office at a time when the physician is normally unavailable, and at that time transmit his data to office unit 102. If the report data includes a specified emergency alarm condition, the physician's home phone number is to be automatically dialed by office unit 102 and the condition is verbally reported.

TIME OF DAY: This is a 4 decimal digit number (0001 to 2359) which is inserted during the patient hookup in order to synchronize local time with the clock associated with patient unit 100.

PATIENT UNIT 100—HARDWARE

Figure 3:
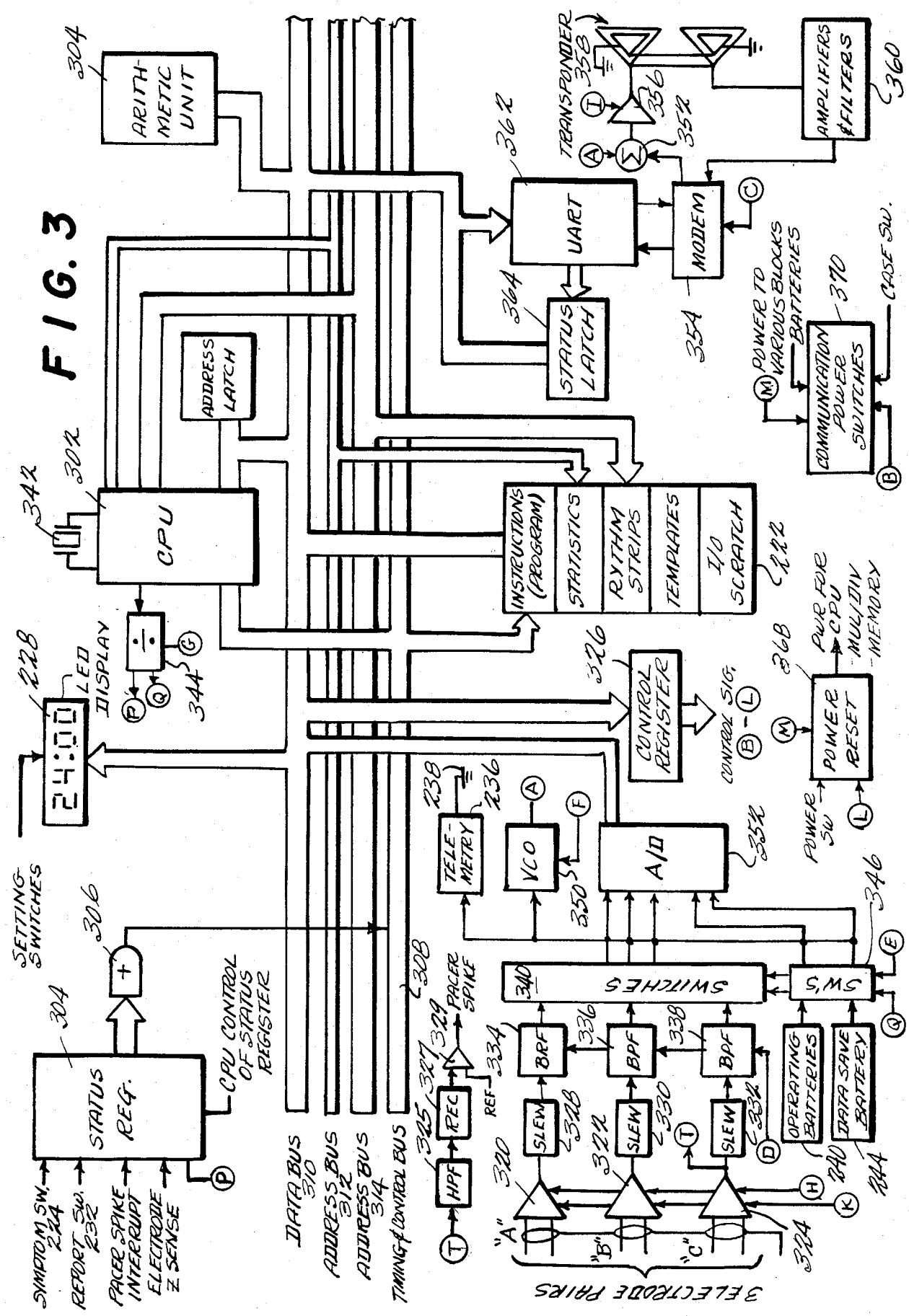
FIG. 3 is a block diagram of the hardware of the preferred embodiment of patient unit 100.

Referring now to FIG. 3 there is shown a block diagram of the hardware of the preferred embodiment of patient unit 100. Patient unit 100 is preferably constructed as a microprocessor-based unit preprogrammed to carry out the specific functions described above in the section of this description entitled FUNCTIONAL DESCRIPTION OF PATIENT UNIT 100. The program for carrying out these functions is stored in an "instructions" section of memory 222. Specifically the program is stored in a volatile Random Access Memory (RAM). A bootstrap loading routine is stored in a more permanent memory-read only memory (ROM) for reloading the program if it is lost due to power failure. A central processing unit (CPU) executes the instructions step-by-step and controls the necessary data manipulations including causing appropriate data manipulations using an arithmetic unit 304. In determining the appropriate next action, CPU 302 obtains information from a status register 304 which indicates the condition of symptom switch 224, report switch 232 and various internal signals including a pacer spike interrupt and an electrode Z sense. The status register signals are coupled to a gate 306 to a timing and control bus 308. Patient unit 100 also includes a data bus 310 and upper and lower order address buses 312 and 314 for accessing various blocks and manipulating data.

Electrodes 108 (shown in FIG. 1) include three electrode pairs forming inputs to channels A, B and C respectively. The channel A input is coupled to an amplifier 320, the channel B is coupled to an amplifier 322 and the channel C is coupled to an amplifier 324. The gain and base line restoration of amplifiers 320, 322, and 324 are controlled respectively by control signals K and H generated by a control register 326. The outputs of amplifiers 320, 322 and 324 are respectively coupled to slew rate limiter circuits 328, 330 and 332. These slew rate detecting and limiting circuits prevent spikes which may appear on the electrodes from being construed as EKG wave forms.

The outputs of slew rate detectors and limiters 328, 330 and 332 are coupled respectively to band pass filters 334, 336 and 338. The bandwidth of these filters is controlled by a control signal D generated by control register 326. The outputs of band pass filters 334, 336 and 338 are coupled to electronic switches 340 which are actuated by control signals Q and E to sample sequentially the signals at the outputs of all three band pass filters. Control signal Q is preferably a 133 or 200 hertz clock signal obtained by dividing the basic clock frequency (represented by crystal 342 of CPU 302 in a series of dividers 344. In essence, signal Q provides a sampling a clock for switches 340. Switches 340 are also controlled by a control signal E generated by control register 326.

The output of amplifier 324 is also filtered by a high pass filter 325 and rectified by a rectifier 327. The rectified signal is compared with a reference level by a differential amplifier 329 to produce a pacemaker spike for patients using a pacemaker. Status register 304 includes a pace spike interrupt.

Operating battery 240 and data save battery 244 were discussed with respect to FIG. 2. Signals from these batteries are coupled to electronic switches 346 also controlled by signals Q and E. Switches 346 effectively sample the condition of batteries 240 and 244. The outputs of switches 340 and 346 represent a multiplexing of the outputs of all three band pass filters and the battery condition signals in time onto a plurality of signal lines coupled to a VCO 350 and an analog to digital (A/D) converter 352 which provides digital signals indicative of the multiplexed signals for coupling to data bus 310. VCO 350 provides an analog FM signal for coupling patient unit 100 signals to a decodalyzer. In parallel with VCO 350 is telemetry 238 (see FIG. 2) for generating an RF Signal. It is presently contemplated that this RF signal at a frequency approximately between commercial television channels 7 and 8.

VCO 350 is controlled by a control signal F generated by control register 326 and provides an output signal A coupled to a summer 352. At summer 352, the VCO signal output is mixed with the signal from a modem 354. The mixed signals amplified by an amplifier 356 and coupled to the transmitting portion of a transponder 358 for coupling a signal onto the telephone line as shown in FIG. 1. Modem 354 is controlled by a control signal C generated by control register 326.

For receiving information, the phone line 106 (shown in FIG. 1) audio tones are coupled to a receiving portion of transponder 358 which develops an electrical signal representative thereof. This signal is amplified by amplifiers and filters 360 and coupled to an input of modem 354. Modem 354 is accessed by a universal asynchronous receiver and transmitter (UART) 362, the status of which is always read by a status latch 364.

Patient unit 100 includes power reset circuitry 368 which is controlled by a control signal L generated by control register 326 and receives power M from communication power management switches 370. Communication power management switches 370 are controlled by a control signal B generated by control register 326. Switches 370 in essence, receive power from batteries 240 and 244 and distributed via "M" to the various circuit block through power reset circuitry 368.

Memory 222, in addition to storing the program for carrying all functions of patient unit 100 includes a "statistics" section for storing trends and distributions including R—R, ST, SPE and PVC as shown in the upper portion of memory 222 in FIG. 2. In addition, memory 222 includes a "rhythm strip" section for storing the eighth second rhythm strips that are obtained either on the basis of asymptomatic criteria or in response to the actuation of patient symptom button 224. The memory also includes a "template" section for storing the various morphological classification of heart beats. This is represented functionally by block 218 in FIG. 2. Memory 222 also includes input/output (I/O) scratch pad memory for temporarily holding data for manipulation by CPU 302.

Of course, this microcomputer based implementation of the functions discussed in the "functional description of patient unit" section of this description represents only the presently preferred exemplary embodiment. It would be possible, using a somewhat larger physical construction to carry out these functions in hard-wired logic discrete circuitry. Regardless of the structural configuration, the functions would be the same.

OFFICE UNIT 102

General Block Diagram

Figure 4A:
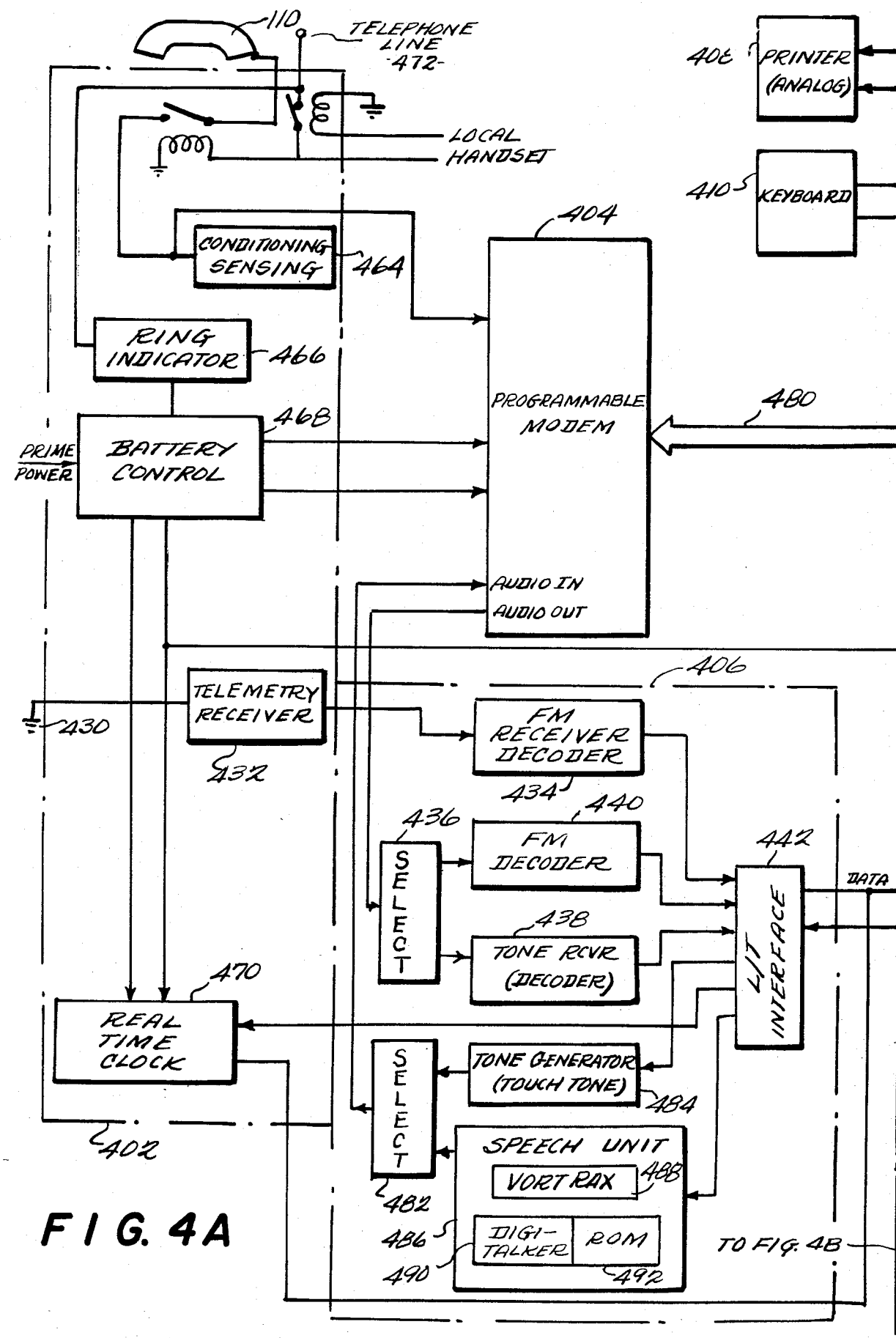
FIG. 4 is a block diagram of office unit 102.
Figure 4B:
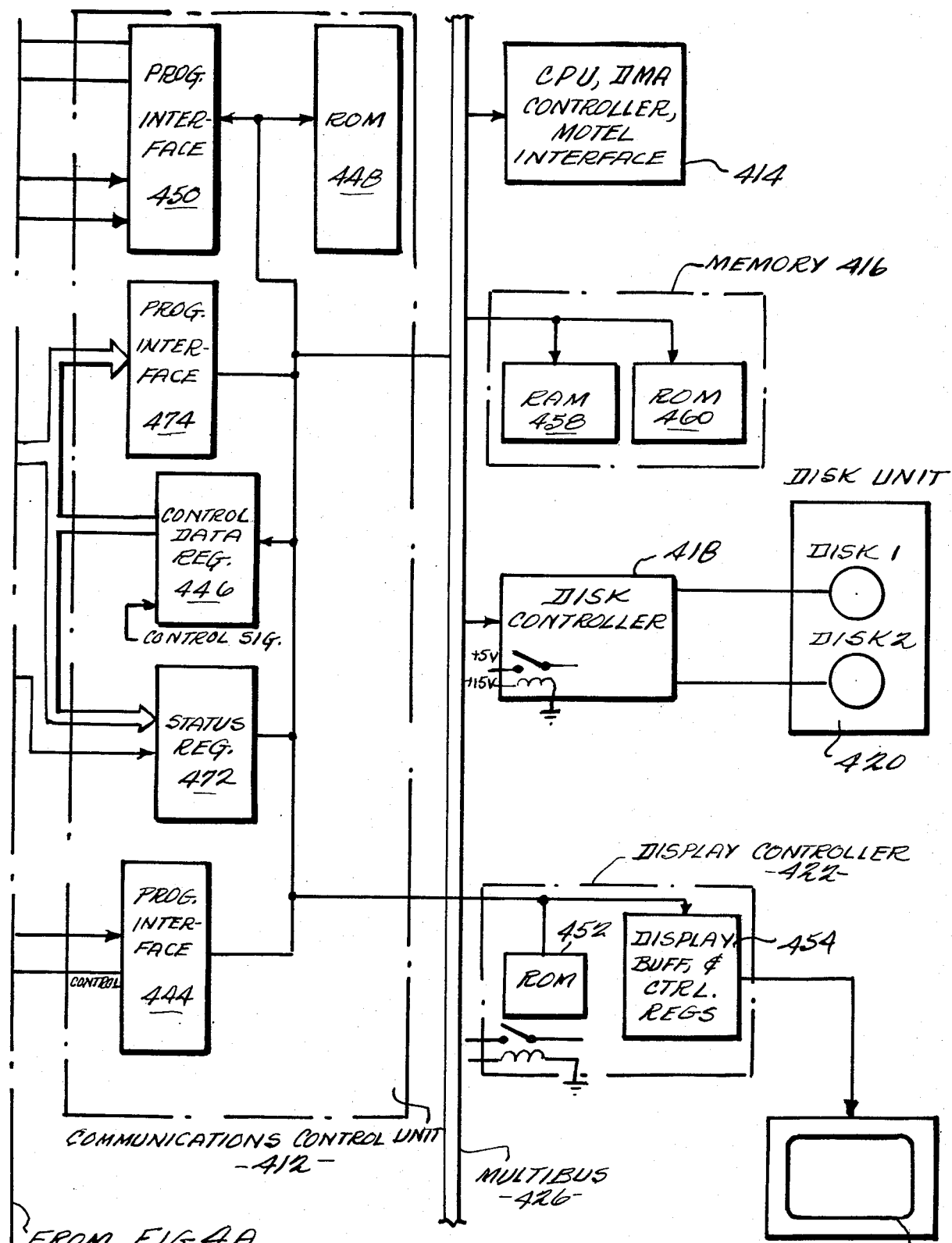

Referring now to FIG. 4 (including FIGS. 4a and 4b), there is shown a block diagram of office unit 102 (shown generally in FIG. 1). Office unit 102 includes the following major blocks: A battery back-up system 402, a programmable modem 404, a listener-talker system 406, a printer 408, a keyboard 410, a communication control unit 412, a CPU, associated controllers and interface 414, a memory 416, a disk controller 418, a disk unit 420, a display controller 422 and a CRT display 424. These blocks are appropriately connected with a multibus 426 and a plurality of individual signal paths and other buses.

Functionally, office unit 102 can accept either on RF input (telemetry) or an acoustic input. Telemetry would be a radio signal telemetered from patient unit 100 via its telemetry circuitry 236 and antenna 238 (both shown in FIG. 2). The telemetered signal would be received by an office unit antenna 430. The received signal is coupled to a telemetry receiver 432 located in battery back-up system 402. As previously discussed, patient unit 100 can output its data in either analog frequency modulated form or in a digital FSK form. Either of these forms can suitably be used through a telephone acoustic coupler or with telemetry. Office unit 102 is capable of decoding information received in either format and received either by telemetry or acoustically.

In essence, telemetry receiver 432 operates as the front end of a receiver including FM receiver decoder 434 located in listener-talker 406. Secondly, office unit 102 can function as part of a frequency shift key (FSK) system in which digital data is transmitted transtelephonically by patient unit 100. For this mode of operation, a selector 436 receives an audio signal from programmable modem 404 and couples it to a tone receiver (decoder) 438 located in listener/talker 406. Thirdly, office unit 102 can operate as part of a frequency modulated (FM) system wherein patient data is used to frequency modulate a carrier. The carrier frequency in the United States is 1800 Hz. The modulation causes a frequency deviation of 12% which is the standard adopted for decodalyzer systems. Essentially, the decodalyzer system is an analog system. Office unit 102 is provided with this capability because many decodalyzer-type systems are in common use and it is desirable to have office unit 102 be compatible with them. For operation in the FM mode, an audio signal from programmable modem 404 is coupled through selector 436 to an FM decoder 440. The outputs of FM receiver decoder 406, FM 440 and tone receiver 438 are coupled to a listener/talker (L/T) interface 442 located within listener/talker system 406. Interface 442 provides data to and receives control from a programmable peripheral interface 444 located in communications control unit 412. Programmable interface 444 is preferably an intel 8255A integrated circuit which couples the data received from interface 442 onto multi-bus 426, to a control data register 446 and from a read only memory (ROM) 448 and to another programmable peripheral interface 450, preferably an intel 8255A. Demodulated or decoded data reaching multi-bus 426 is coupled to display controller 422 and stored in a read only memory (ROM) 452 contained therein. The data is also coupled to displyy buffer and control registers 454 for ultimate display by CRT display 424.

Data can also be stored on and read from disk unit 420 including disk 1 and disk 2 via disk controller 418 also coupled to multi-bus 426.

Memory 416 includes a random access memory (RAM) 458 and a read only memory (ROM) 460 providing low level controls for various functional blocks of office unit 102 including its disk controller and display controller. The actual program instructions are stored on disk unit 420. This includes a patient hook-up program for interactively communicating with the physician or other hook-up personnel for entry of particular data characterizing event recording criteria, alarm criteria, patient data, etc. for the particular patient being hooked up and identifying the particular test that is about to take place. Memory 416 may also contain data received from patient unit 100.

Returning to battery back-up system 402, this system, in addition to the telemetry receiver 432 includes the following sub-systems: A condition sensing circuit 464, a ring indicator 466, a battery control circuit 468 and a real time clock 470. Condition sensing circuits 464 sense the condition of telephone relays and together with ring indicator 466, a battery control circuit 468 and a real time clock 470. Condition sensing circuits 464 sense the condition of telephone relays and together with ring indicator 466 manage the answering and hanging up of a telephone line 472 dedicated to office unit 102. Office unit 102 is equipped with back-up batteries that are monitored by battery control 468. In essence, battery control 468 is coupled to a source of prime power and to the back-up batteries and provide a reliable source of D.C. power to modem 404 and other blocks of the office unit. During a power failure, battery control circuit 468 will provide an appropriate signal to modem 404 so that patient unit 100 callers may be given a verbal message via listener/talker 406 if office unit 102 is unable to accept and process data. The back-up batteries will be used to provide these messages to callers and to save any data already accepted by office unit 102. Real time clock 470 provides an indication of the time that data is received for print-out on the patient report prepared by printer 408.

Communications control unit 412 effectively controls communications to and from office unit 102. Unit 412 includes programmable interface 450, ROM 448, a control data register 446, programmable interface 444 and a status register 472 and another programmable communication interface 474. Programmable interface 450 provides data and control signals to printer 408 and receives data and control signals to printer 408 and receives data and control signals from keyboard 410. In essence the interactive communication that occurs between office unit 102 and personnel hooking up the patient is carried out via keyboard 410 and display 424. Various instructions and menu selection appear on display 424 and appropriate instructions, requests, and selections are made by pressing the various keys of keyboard 410. Communication between programmable modem 404 and communication control unit 412 occurs via a bus 480. This bus carries various control and information signals for carrying out communication control. For example, such signals include control signals indicating that office unit 102 is prepared to receive or send data, signals indicating whether the office unit telephone is "off hook" ringing, or receiving a dial tone, and signals to force an answer of the telephone.

Listener/talker 406, in addition to decoder 434, decoder 440, receiver 438, selector 436 and listener/talker interface 442 also includes a selector 482, a tone generator 484 and a speech unit 486. Speech unit 486 includes a vortrex 488, a digitalker 490 and a read only memory 492 associated with the digitalker for storing various words for verbal communication. In essence, speech unit 486 enables office unit 102 to meaningfully talk to a patient who has called in to transmit data. Tone generator 484 is capable of generating the appropriate touch-tones to dial out to call a physician. Generator 484 would be used in a case where office unit 102, having determined that cetain data must be communicated to the physician, dials the physician's home phone 114 (see FIG. 1).

Keyboard 410

Figure 5:
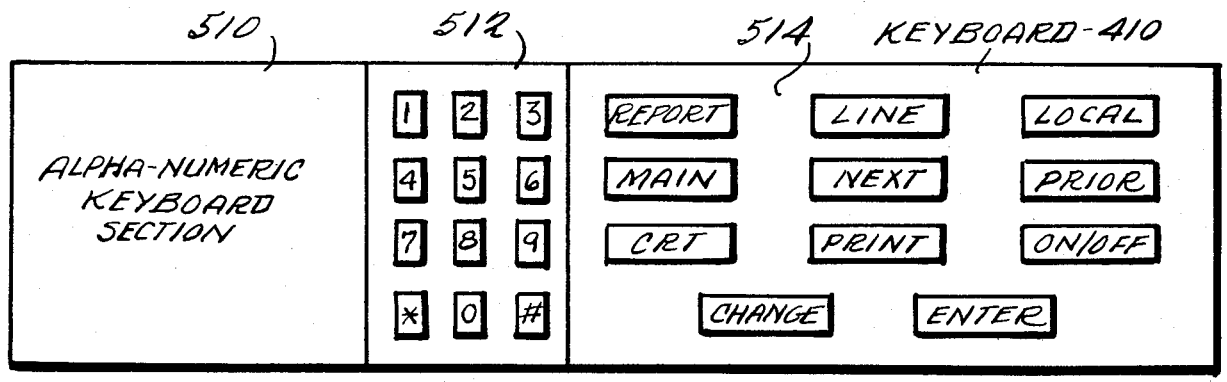
FIG. 5 is a block diagram of keyboard 410, shown as a general block in FIG. 4.

Referring now to FIG. 5 there is shown a more detailed block diagram of keyboard 410 shown as a general block in FIG. 4. Keyboard 410 includes three sections: an alpha numeric keyboard section 510, a telepad section 512 and a function key section 514. Alpha numeric keyboard section 510 includes the standard keys found on most typewriter or general purpose computer keyboards. Telepad section 512 includes the buttons generally found on Touch Tone telephones. Function key section 514 includes the following eleven function keys: REPORT, lINE, lOCAL, MAIN, NEXT, PRIOR, CRT, PRINT, ON/OFF, CHANGE and ENTER.

The REPORT, LINE and LOCAL keys are telephone control keys. Pressing the LOCAL key takes the office unit handset off-line and connects it to the office unit so that the patient can be hooked up. To take an incoming telephone call, it is necessary to press the LINE key to connect the office unit to the telephone line. Pressing the REPORT key allows the office unit to take a patient report.

The MAIN, NEXT and PRIOR keys are for menu selection. Patient hook-up proceeds in an interactive manner. The office unit asks the physician or hook-up technician for specific data to customize the monitoring test for the patient being hooked up. The type of data required is set forth in the hook-up report near the end of this description. The data is requested in the form of specific options presented in a plurality of menus. The menus are screen presentations on CRT 424 which present alternative choices and which present specific blank spaces to be filled in by the hook-up personnel with patient or criteria data. By pressing the MAIN key, the operator can return from any menu currently being displayed on CRT 424 to the main menu. The NEXT key, allows him to step from the menu currently being displayed to the next menu in the sequence. The PRIOR key allows him to step from the menu currently being displayed to the previous menu in the sequence.

The CRT key on the third row of keys of section 514 is a two-position scrolling control switch. A first position of this key moves the EKG on the screen of display 424 from right to left (it scrolls). In a second position of the key the EKG freezes at its current position.

The "PRINT" key activates printer 408 to obtain a hard copy of whatever appears on the face of CRT display 424. The "ON/OFF" key is used to turn the CRT screen on or off.

The "CHANGE" and "ENTER" are used respectively to change or enter patient or criteria data for a particular category that may appear in a menu currently displayed on CRT display 424. Specific numerical information for patient or criteria data can be entered by pressing the appropriate keys of the telepad section 512 of keyboard 410. Telepad section 512 includes an asterisk (*) for changing a parameter, such as high rate, and a pound sign key (#) for entering a new parameter.

Office unit 102 is a microprocessor based unit and operates in accordance with program and data information stored in memory 416. Specific data pertaining to the patient may be stored in memory 416 or on disks 1 and 2, recalled by the microprocessor by reference to a transmitted patient identification number and incorporated into the printed patient report. CPU 414 is used to control formatting of the data received from a patient unit, converting incoming binary numerical data to decimal form, etc. etc. Repetitive headings are stored in microprocessor memory and are called out by the incoming digital information as required. This facility of course implies that the patient unit 100 program has encoded appropriate control characters (or character groups) which are serially transmitted along with the output data, and that the microprocessor decodes these characters and formats the data accordingly.

During the time office unit 102 is printing one patient report, another patient may call in a second report. Office unit 102 contains sufficient memory for storing multiple patient reports in its disk storage. It is not necessary for office unit 102 to fully prepare a patient report for data dumped by a patient before it can accept another patient report. It can keep accepting data from one patient after another and que the data until there is time to prepare the patient reports.

One of the more significant functions of the office unit microprocessor is to recognize the occurrence of an emergency notification condition. It must then synthesize an appropriate notification message, dial the physician's emergency phone number using tone generator 484 and verbally transmit the alarm message to the physician.

Printer 408 prepares the printed patient report in finished form on standard sized, sprocketed, thermal paper. It is capable of fully unattended operation providing sufficient paper has been preloaded into it. Printing speed will be about 12 seconds per page. The quality of any EKG recording prepared by printer 408 is as good as that of a conventional hot stylus pen recorder. By operation of the PRINT key on the control keyboard, any data on the face of the office unit CRT can be transferred to a "hard copy" for later reference by the physician.

Disk unit 420 including disks 1 and 2 is used to store alphanumeric data specific to a given patient, and his physician. This data can be called into office unit 102 memory by referencing to the patient identification number recorded on the disk. In general, this data will be used as the preface to the printed report. The disk can accommodate such data for many patients.

Under certain conditions such as a failure of printer 408, disk unit 420 may be used to provide an intermediate storage of a patient report until repair has been completed.

During the period of operational test of both patient unit 100 and office unit 102, the programs for both of these units are stored on a disk. This provides a convenient, easily alterable, storage medium for loading both of these computer programs into their appropriate RAM storages.

Office unit 102 incorporates speech unit 486 for generating verbal messages so that it can directly "speak" to the physician or patient (and possibly a maintenance man). This same capability permits the interactive data insertion "dialogue" to incorporate both visual and verbal requests for control and patient data. The primary function of the speech facility, however, is the generation of specific alarm messages which the physician has himself requested. Such messages can then be communicated verbally to the physician if the patient transmits a report to the office unit 102 at a time when the physician is normally unavailable.

In an automatic answering and dialing mode, the office unit 102 automatically "picks up" if the patient transmits a report to a dedicated telephone number. Printer 408 is able to handle the possibility of wrong numbers. If an emergency alarm condition which has been inserted by the physician actually occurs during the patient test, and is then transmitted and recognized, the physician's emergency phone number is automatically dialed and an appropriate verbal message is communicated under the security conditions previously specified by the physician.

Patient Hook-up

To begin a cardiac monitoring test, the patient must be hooked up to a patient unit 100. Electrodes 108 are attached to the patient's body and then the integrity of the electrode hook-up is checked. As previously pointed out, patient unit 100 can communicate by either telemetry or acoustic coupling. The acoustic coupling can be direct to an office unit 102 or via a standard voice telephone line. If the physician does not have an office unit 102, acoustic outputs of patient unit 100 can be appropriately modulated and used to drive standard EKG equipment in order to visualize the EKG signal and assure electrode hookup integrity.

After the electrodes are in place, the phsycian can place his office unit in a local mode and begin to program the various analyzation, event recording and alarm criteria for this particular patient into patient unit 100. The criteria is set forth in detail in the hook-up report set forth later in this description. The hook-up is managed by a hook-up program stored in office unit 102 which controls the display on CRT 424 of several menus, each menu having various parameter classifications to be selected. Specific data can be entered using the alpha numeric keyboard section 510 and telepad section 512 of keyboard 410 shown in criteria is not programmed into patient unit 100, preprogrammed default will be used.

Whether or not data is being entered to replace the default data programmed into patient unit 100, the patient unit can transmit the EKG signals developed on all three channels to the physician's office unit 102 or to conventional EKG visualizing equipment.

Menus

The following is the presently preferred text of the menus that appear on the face of CRT display 424 during patient hook-up. These menus indicate the types of analysis, modification and event recording criteria that are used by the patient unit.

MAIN MENU

1. Ambulatory Monitoring
2. Event Telemetry
3. Cardio Beeper Reception
4. Special Programs
5. Stand-by This menu allows the physician to select the operational mode:

1—Hook-up and enroll a patient.
2—Receive telemetered EKG strips from patient.
3—Office Unit will emulate a decodalyzer and can receive live transmissions from Cardio Beeper or Patient Unit.
4—Operate edit program and any other special functions.
5—Prepare Office Unit for automatic reception of patient report.

| PATIENT INFORMATION | |
|---|---|
| Patient Name | _____ |
| Phone # | _____ |
| ID/SSN | _____ |
| Age: ____yrs. Sex: | _____ |
| Height ____ft/in. Weight ____lbs | |
| Address | _____ |
| Hospital: | _____ |
| Address: | _____ |
| Room # | _____ |

A physician can choose to store a complete patient record with the patient report by filling in all of the Patient Information. Otherwise, only the items deemed "critical" (items listed below) must be keyed to guarantee proper identification of the report.

| | |
|---|---|
| Patient Name | Physician name |
| Phone Number | Office Phone Number |
| Hookup Date | Other Phone Numbers |
| Hookup Time | |

| OMINOUS PHENOMENA | |
|---|---|
| St Elevation Change Limit: | 1.5 MM |
| ST Depression Change Limit: | 1.5 MM |
| PVC Limit: | 6 BPM |
| R on T Limit: | 0.25 Secs |

The physician can select his own criteria for identifying more serious phenomena.

| RATE CRITERIA | |
|---|---|
| Pause: | 1.5 Secs |
| Missed Beat: | 2.2 Secs |
| Low Rate Run: | 45 BPM |
| Couplet Rate: | 140 BPM |
| High Rate Run: | 130 BPM |

The physician can customize the system to identify conditions based on his own criteria. Default values are stored in the unit which can be left as is, if the physician so chooses.

| PATIENT INFORMATION (Continued) | |
|---|---|
| Patient Symptoms: | _____ |
| | _____ |
| | _____ |
| Medical History: | _____ |
| | _____ |
| | _____ |
| | _____ |

| PATIENT INFORMATION | |
|---|---|
| Physician Name: | _____ MD |
| Address: | _____ |
| | _____ |
| Office Phone #: | _____ |
| Other Phone #'s: | _____ |
| | _____ |
| | _____ |

| REPORT INFORMATION | |
|---|---|
| Reason for Report: | _____ |
| Hookup Date: _____ Time: | _____ |
| Hookup Location: | _____ |
| Hooked up by: | _____ |

| REPORT FORMATS | |
|---|---|
| Standard Format (Y/N): | Y |
| STI Logo (Y/N): | Y |

| REPORT FORMATS | |
|---|---|
| -continued | |
| Custom Logo (Y/N): | N |
| Section Deletions (Underline) B,C,D,E,F,G,H,I,J,K,L,M,N,O | |

The physician can use the edit function to modify the format of the report. Detailed sections of the report can be eliminated, if a more consolidated format is desired. A customized logo can also be selected for the heading.

| PERIODIC SAMPLING | |
|---|---|
| P-Wave (Y/N): | Y |
| Interval Between Samples (30, 60, or 120): | 120 Mins |
| Routine Strips (Y/N): | Y |
| Interval Between Strips (1, 2, or 4) | 4 Hrs |

Periodic samples can be taken on a regular interval (ex:hourly). These samples can be p-wave (1 second strips) samples or routine strips (8 seconds) or both.

| NOTIFICATIONS | |
|---|---|
| Rate (Y/N): | N |
| PVC (Y/N): | N |
| Ectopic Run (Y/N) | N |
| ST Changes (Y/N) | N |
| Call Physician Automatically (Y/N): | N |

The physician can select any condition under which he would want notification from the patient. The physician can also enable an option which will generate an automatic call to the doctor in the event of an ominous phenomena on the final report.

PATIENT UNIT NOW LOADED

Control Program=100.0 Version: 01
Battery Voltage=6.0 Volts
Data Save Battery=OK
Anticipated Operating Time=72 HRS
Push "next" to continue with electrode hookup.

After all of the previous criteria have been selected the patient unit is tested. The version of software and the level of battery strength are both checked, and the results posted to the screen.

| MAXIMUM NUMBER OF EVENT RECORDINGS | |
|---|---|
| Pacemaker Failures: | 5 |
| ST Changes: | 5 |
| Ectopic Runs: | 5 |
| Tachyarrhythmias: | 5 |
| Bradyarrhythmias: | 5 |
| Symptomatics: | 5 |
| New Morphologies: | 1 |
| Channel Selection (1, 2 or 3) | 3 |
| Recording Frequence Response (AHA = A, MONITORING = M): | M |

The physician can select the maximum number of strips which he wants recorded under each condition. These selections allow for a more consolidated report in which the physician limits the number of examples of any individual condition.

| PACEMAKER FAILURE ANALYSIS | |
|---|---|
| Implanted Pacemaker (Y/N): | N |
| Pacemaker "Automatic" Rate: | BPM |
| VVI Pacemaker (Y/N): | Y |

If the patient has an implanted pacemaker, the physician can instruct the unit check for pacemaker failures. The patient's pacemaker automatic rate must be entered to permit this analysis.

HOOK-UP REPORT

After patient hook-up, office wait 102 can prepare a hook-up report that summarizes all data that has been set up during the hook-up procedure. The presently preferred format of a patient hook-up report follows.

| BASELINE (HOOK-UP) REPORT | |
|---|---|
| 1. Report No.: | DATE: |
| 2. Patient Information | |
| Name | |
| Address | |
| | |
| Phone No. | |
| Patient Data: Age ____ Sex ____ | |
| Height ____ Weight ____ | |
| Hospital _____ | |
| _____ Room No. ___ | |
| Patient ID/SSN | |
| Recorder No. | |
| 3. PHYSICIAN INFORMATION | |
| Name | |
| Address | |
| | |
| | |
| Office Phone No. | |
| Other Phone Nos. ____ | |
| 4. REPORT DATA | |
| Reason for Report | |
| Date of Hookup | |
| Time of Hookup | |
| Hooked Up By | |
| 5. PATIENT SYMPTOMS (3) | |
| | |
| | |
| | |
| 6. MEDICAL HISTORY | |
| | |
| | |
| | |
| | |
| 7. MONITORING CRITERIA | |
| 1. Pause | ____Seconds |
| 2. Missed Beat | ____Seconds |
| 3. Low Rate Run | ____BPM |
| 4. Couplet Rate | ____BPM |
| 5. High Rate Run | ____BPM |

-continued

Figure 6:
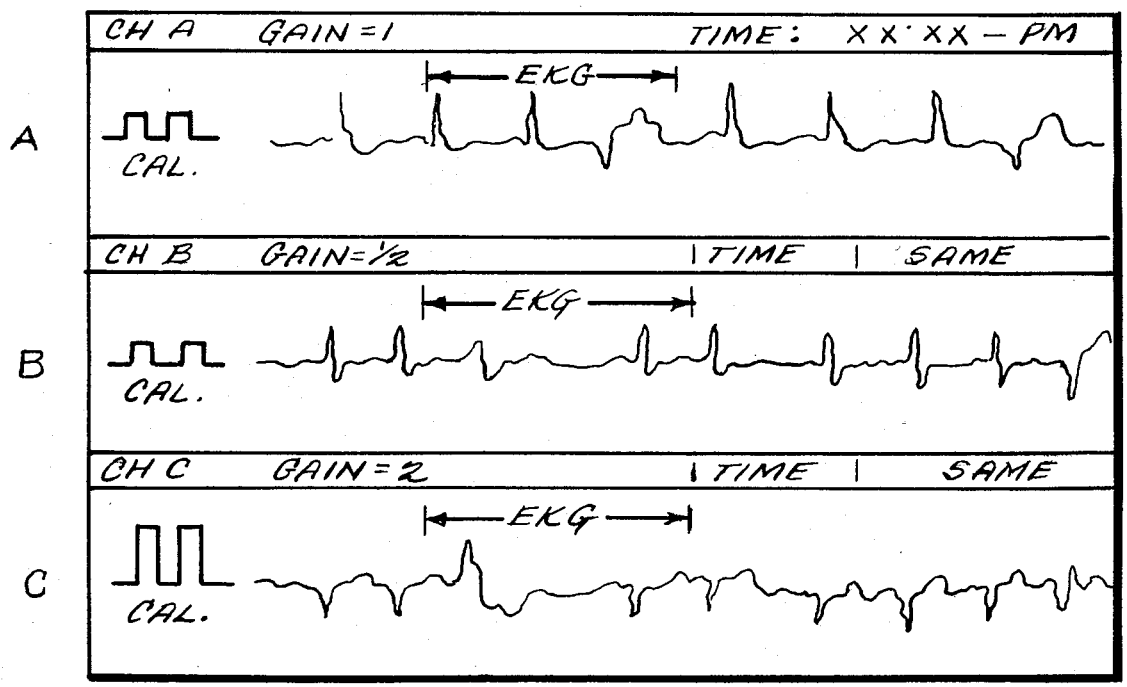
FIG. 6 is a diagram of EKG rhythm strips format in the hook-up report showing waveforms of symbolic data.

| BASELINE (HOOK-UP) REPORT | | |
|---|---|---|
| 6. (POS) ST Elevation Limit | | MMS |
| 7. (NEG) ST Depression Limit | | MMS |
| 8. PVC Limit | | BPM |
| 9. RonT Limit | | MSEC. |
| 10. Implanted pacemaker (Y/N) | | |
| 11. Pacemaker Rate | | BPM |
| 12. Max. No. Event Recordings | | |
|    a. Pacemaker Failures | | |
|    b. ST Changes | | |
|    c. Ectopic Runs | | |
|    d. Tachyarrhythmias | | |
|    e. Bradyarrhythmias | | |
|    f. Symtomatic | | |
| 13. P-wave Sampling (Y/N) | | |
| (If 13 = Y) a. Interval between samples | | mins. |
|    b. Max. No. Samples | | |
| 14. Normal Sampling (Y/N) | | |
| (If 14 = Y) a. Interval Between Samples | | min. |
|    b. Max/ No. Samples | | |
| 15. Notifications (Y/N) | | |
| (If 15 = Y) a. Rate | | |
|    b. PVC's | | |
|    c. Ectopoc Runs | | |
|    d. ST Changes | | |
| 16. Event Telemetry (Y/N) | | |
| 17. Channels Active | | |
| 18. Call Physician if alarm (Y/N) | | |
| 19. Emergency Phone No. | | |
| 8. EKG RHYTHM STRIPS [See FIG. 6 for the format of EKG Rhythm Strips] | | |

PATIENT ACTIVITY & SYMPTOM DIARY
(Patient keeps this log during his test)

| Time | Activity | Symptom |
|---|---|---|
| 7: ____AM | | |
| 8: ____ | | |
| 9: ____ | | |
| 10: ____ | | |
| 11: ____ | | |
| 12: ____ | | |
| 1: ____PM | | |
| 2: ____ | | |
| 3: ____ | | |
| 11: ____ | | |
| 12: ____ | | |
| 1: ____AM | | |
| 2: ____ | | |
| 3: ____ | | |
| 4: ____ | | |
| 5: ____ | | |
| 6: ____ | | |
| 7: ____AM | | |

PATIENT REPORT

When a patient phones to office unit 102 and dumps data from a test, office unit 102 prepares the patient report. The presently preferred format is set forth below. In various places throughout the report, in order for it to present a meaningful format, symbolic or hypothetical data is used. The data shown is not intended to create a self-consistent report but rather is only used for illustrative purposes.

PATIENT REPORT

A.
Patient Name _____ Report No. ____
Patient Address _____
Physician Name _____
Test Start: Date ____ Time ____
Test Complete: Date ____ Time ____

B.
Duration of Test: ____Hrs. ____mins.
Recorder Serial Number _____
Satisfactory Signal: Ch.A . ____%
                 Ch.B. ____% Ch.C ____%

Figures 7, 9:
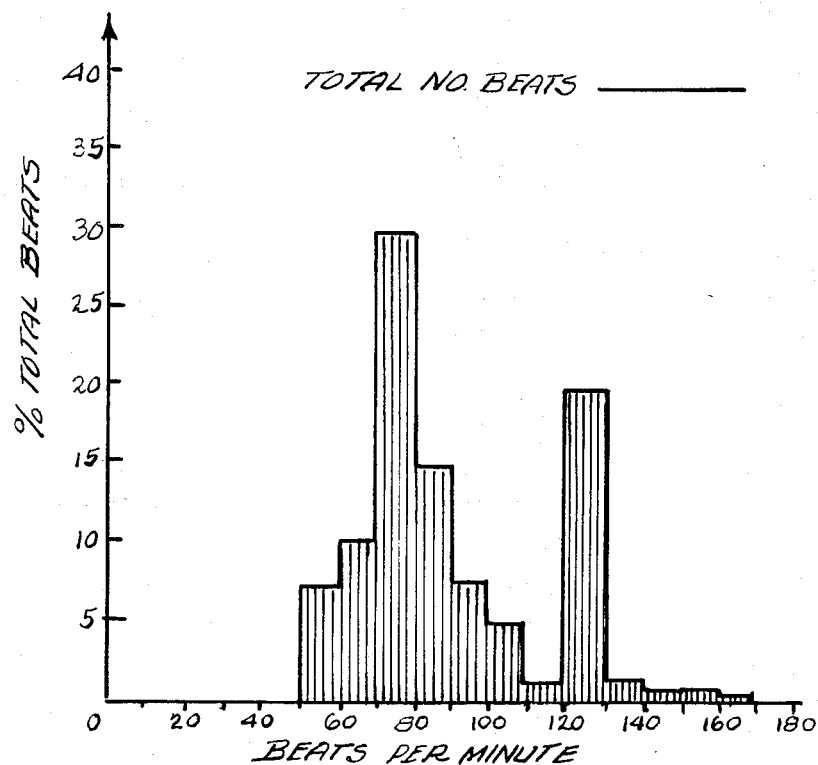
FIG. 7 is a diagram of the beat classification from the patient report showing waveforms of symbolic data.
FIG. 9 is an RR rate histogram from the patient report graphically depicting symbolic data for the purpose illustration only.

C.
REPORT SUMMARY
1. Beat Classification
[See FIG. 7 for the form of the beat classification presentation]

2. Rate Information
Highest Rate ____BPM; Family ____; Time ____;
Sample No. ____
Lowest Rate ____BPM; Family ____; Time ____;
Sample No. ____
Average Rate (Dominant Morphology) ____BPM;
Sample No. ____

D. Sample Summary Group
........................Sample
Time Recording Criteria & Duration Sympton Familie
   s          No.
       High Couplet/2 sec.
       New Morphology/8 sec.
       Normal Sample/8 sec.
       P-wave Sample/1 sec.
       Symptom/High Couplet Rate/8 sec.
       Symptom/High Couplet Rate/8 sec.
       P-wave Sample/1 sec.
High Couplet Rate
*Physician notified ____Date
Time ____
Physician
Comment _____

_____Signature_____

Figure 8:
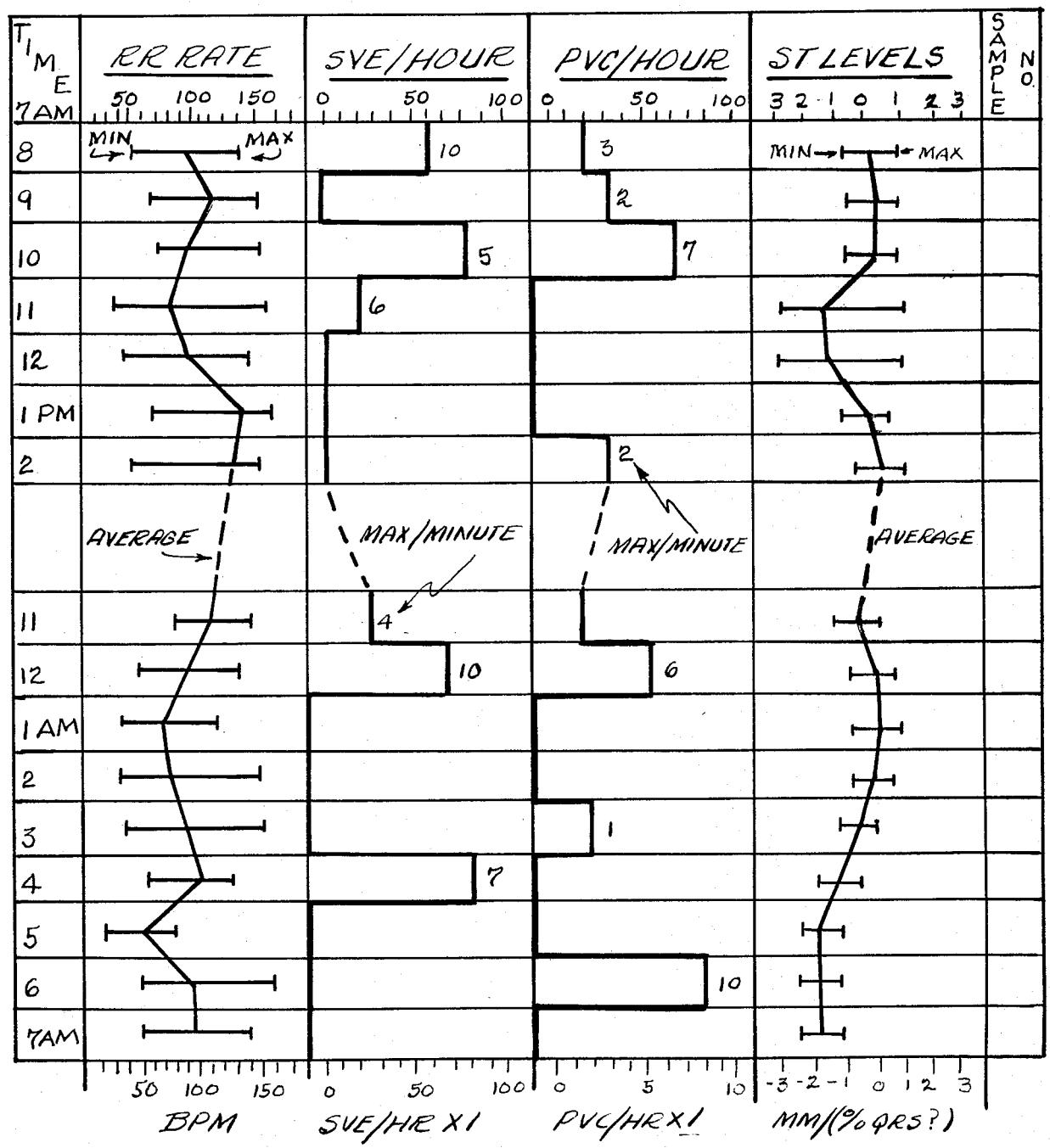
FIG. 8A and 8B are monitoring profiles from the patient report including symbolic data for illustrative purposes only.

E. Monitoring Profile
[See FIG. 8 for the format and a hypothetical example of a monitoring profile]
F. RR Rate Histogram/2H Hours (all Beats)
[See FIG. 9 for the format of the RR rate histogram]
DOMINANT RHYTHM - RR RATE DISTRIBUTION/HOURS
BEATS/MINUTE[(1)]

| Time | 40 | 40–60 | 60–80 | 80–100 | 100–120 | 120–140 | 140 | Hourly Total | Hourly Un-usable |
|---|---|---|---|---|---|---|---|---|---|
| 7 AM | | | | | | | | | |
| 8 | | | | | | | | | |
| 9 | | | | | | | | | |
| 10 | | | | | | | | | |
| 11 | | | | | | | | | |
| 12 | | | | | | | | | |
| 1 PM | | | | | | | | | |
| 2 | | | | | | | | | |
| 3 | | | | | | | | | |
| 11 | | | | | | | | | |
| 12 | | | | | | | | | |
| 1 AM | | | | | | | | | |
| 2 | | | | | | | | | |
| 3 | | | | | | | | | |

PATIENT REPORT 4
5
6
7 AM
TOTALs

HOURLY RR RATE DISTRIBUTION

Estimated by TIME

| Time | 40 | 40–60 | 60–80 | 80–100 | 100–120 | 120–140 | Record ED 140 | Estimated ED Hourly Total | Hourly Un-usable |
|---|---|---|---|---|---|---|---|---|---|
| 2–3 PM | | | | | | | | | |
| 3–4 | | | | | | | | | |
| 4–5 | | | | | | | | | |
| 5–6 | | | | | | | | | |
| 7–8 | | | | | | | | | |
| 8–9 | | | | | | | | | |
| 9–10 | | | | | | | | | |
| 10–11 | | | | | | | | | |
| 11–12 | | | | | | | | | |
| 12–1 PM | | | | | | | | | |
| 1–2 | | | | | | | | | |
| 2–3 | | | | | | | | | |
| 3–4 | | | | | | | | | |
| 4–5 | | | | | | | | | |
| 5–6 | | | | | | | | | |
| 6–7 | | | | | | | | | |
| 7–8 | | | | | | | | | |
| 8–9 | | | | | | | | | |
| 9–10 | | | | | | | | | |
| 10–11 | | | | | | | | | |
| 11–12 | | | | | | | | | |
| 12–1 PM | | | | | | | | | |
| 1–2 | | | | | | | | | |
| Totals | | | | | | | | | |

H. Ectopic Run Data

| Show | Time | Number of Beats | Duration (secs) | Sample Number | Total Runs/HR |
|---|---|---|---|---|---|
| | 7:20 AM | | | | |
| | 8:50 AM | | | | |
| | 10:40 AM | | | | |
| | 10:51 AM | | | | |
| | 11:04 PM | | | | |
| | (2)3:09 PM | | | | |
| | 3:12 PM | | | | |
| | 3:21 PM | | | | |
| | 3:47 PM | | | | |
| | 3:51 PM | | | | |
| | 3:52 PM | | | | |
| | 3:54 PM | | | | |
| | 3:55 PM | | | | |
| | 5:15 PM | | | | |
| | 11:45 AM | | | | |
| | 2:21 AM | | | | |
| | 2:42 AM | | | | |
| | 2:53 AM | | | | |
| | 5:07 AM | | | | |
| TOTALS | | | | | |

SCAN TECH: _____

Figure 10:
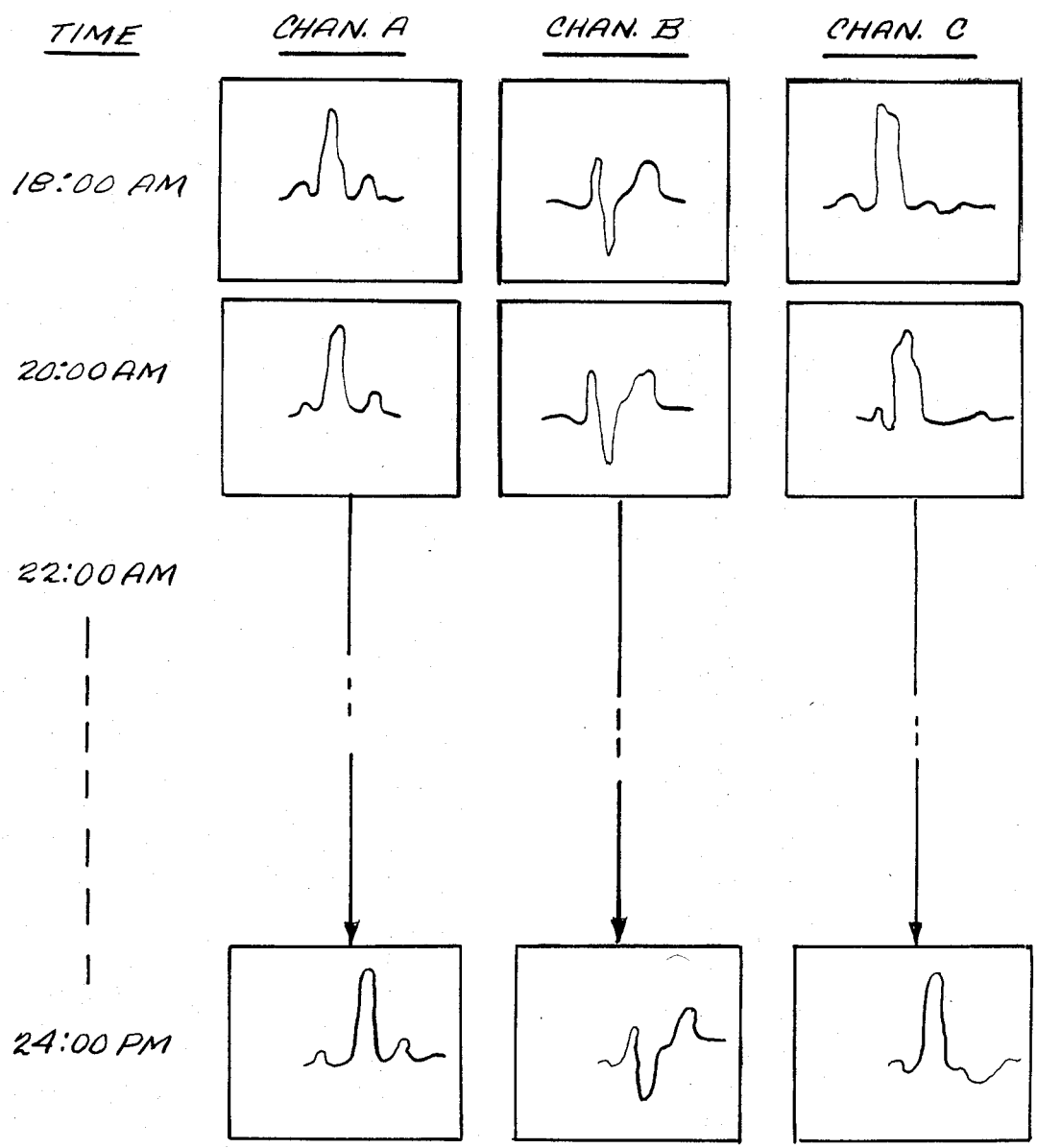
FIG. 10 is a diagram of the P-wave samples from the patient report graphically showing symbolic data for illustrative purposes only.

I. P-wave Samples
[See FIG. 10 for the format of the P-wave samples]
J. ST changes
ST changes waveforms are presented substantially in the same format as the p-wave samples shown in FIG. 10.
K. Prematurity and Postmaturity Data
[See FIG. 11 for the format of the prematurity and postmaturity data]
L. Pacemaker Failures
[See FIG. 12 for the format of the presentation of Pacemaker Failure Data]
M. Symptomatic Recordings
Data indicative of symptomatic recordings are presented substantially in the same format as used for presenting pacemaker failures in FIG. 12.
N. Routine Samples
Data indicative of routine samples (taken periodically) are presented substantially in the same format as that for indicating pacemaker failures in FIG. 12.
O. Criteria recordings
Data indicative of criteria recordings are presented substantially in the same format as that for indicating pacemaker failures in FIG. 12.

[1] Assumes 12 c = 5
[2] Max. of 8/hour in spec, after which only total count is accumulated While the invention has been described in connection with what is presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

We claim:

1. A cardiac monitoring system for monitoring an ambulatory patient, comprising:

a cardiac monitoring patient unit for the ambulatory patient comprising:

means operatively connectable with a patient's body for providing an EKG signal indicative of electrical activity associated with a patient's heart action;

means for sampling the EKG signal provided by the EKG signal providing means to provide a plurality of EKG signal samples;

signal processing means for analyzing the EKG signal samples in real time and according to predetermined criteria and generating, as a result of that analysis, processed data including a plurality of cardiac events and statistics related to all heartbeats occurring during a predetermined monitoring period, for inclusion in at least a portion of corresponding patient report intelligible to a person skilled in coronary care;

memory means for storing the processed data generated by the signal processing means;

portable housing means, suitable for being worn or carried out by the patient, containing the sampling means, signal processing means and memory means;

patient actuable transmitting means for causing data including the processed data stored in the memory means to be read from the memory means and to be transmitted over a communication channel; and office unit means for cooperative use with said patient unit, said office unit means having means for automatically and without the necessity of any human operator, receiving the processed data via the communication channel, means for automatically and without the necessity of any human operator comparing the processed data with predetermined medical personnel notification criteria, and means for automatically and without the necessity of any human operator notifying medical personnel if the predetermined medical personnel notification criteria is satisfied so that the medical personnel can intervene in an appropriate medical situation, said office unit means including means for preparing the corresponding patient report based upon the received processed data.

2. A system according to claim 1 wherein said office unit means includes means for transmitting to the patient unit via the communication channel asymptomatic event recording criteria, the memory means of the patient unit including means for storing the asymptomatic event recording criteria transmitted via the communication channel by the transmitting means of the office unit means, the signal processing means of the patient unit including means for analyzing the EKG signal samples with respect to the asymptomatic event criteria and causing the event to be stored if any of the criteria are met.

3. A system according to claim 1 wherein the office unit means comprises means for transmitting to the patient unit via the communication channel patient notification criteria, the memory means of the patient unit including means for storing the patient notification criteria transmitted via the communication channel by the transmitting means of the office unit means, the portable housing means of the patient unit having associated therewith patient notification means, the signal processing means of the patient unit including means for analyzing the EKG samples with respect to the patient notification criteria stored in the associated memory means and causing said patient notification means to be actuated if any of the patient notification criteria are met.

4. A system according to claim 1 wherein said patient actuatable transmitting means is mounted within said portable housing means and the communication channel thereof is a standard voice-grade telephone channel, said patient actuatable transmitting means also including telemetry means for transmitting by telemetry data stored in the memory means and the EKG signal provided by the EKG signal providing means, the office unit means further including means for receiving stored data and EKG signal transmitted by telemetry by the telemetry means of said patient unit.

5. A system according to claim 1 wherein said EKG signal providing means includes means providing three different EKG channel signals indicative of electrical activity associated with a patient's heart action, said sampling means including means for sampling each of the three channel signals provided by the EKG signal providing means, said signal processing means including means for substantially simultanously analyzing the samples of all three channels provided by said sampling means in real time and according to predetermined criteria so as to obtain enhanced waveform analysis.

6. A system according to claim 1 wherein the office unit means comprises means for transmitting to the patient unit via the communication channel predetermined analyzing criteria to be used by the signal processing means and wherein the memory means of the patient unit includes means for storing the analyzing criteria so transmitted.

7. A system according to claim 6 wherein said office unit means includes means for transmitting to the patient unit via the communication channel asymptomatic event recording criteria, the memory means of the patient unit including means for storing the asymptomatic event recording criteria transmitted via the communication channel by the transmitting means of the office unit means, the signal processing means of the patient unit including means for analyzing the EKG signal samples with respect to the asymptomatic event criteria and causing the event to be stored if any of the criteria are met.

8. A system according to claim 6, 2, 4, 5 or 7 wherein the office unit means comprises means for transmitting to the patient unit via the communication channel patient notification criteria, the memory means of the patient unit including means for storing the patient notification criteria transmitted via the communication channel by the transmitting means of the office unit means, the portable housing means of the patient unit having associated therewith patient notification means, the signal processing means of the patient unit including means for analyzing the EKG samples with respect to the patient notification criteria stored in the associated memory means and causing said patient notification means to be actuated if any of the patient notification criteria are met.

9. A system according to claim 2, 3, 5 or 7 wherein said patient actuatable transmitting means is mounted within said portable housing means and the communication channel thereof is a standard voice-grade telephone channel, said patient unit further including telemetry means for transmitting by telemetry the EKG signal provided by the EKG signal providing means for aiding in patient hook-up of the patient unit.

10. A system according to claim 9 wherein the office unit means comprises means for transmitting via the communication channel patient notification criteria, the memory means of the patient unit including means for storing the patient notification criteria transmitted via the communication channel by the transmitting means of the office unit means, the portable housing means of the patient unit having associated therewith patient notification means, the signal processing means of the patient unit including means for analyzing the EKG samples with respect to the patient notification criteria stored in the associated memory means and causing said patient notification means to be actuated if any of the patient notification criteria are met.

11. A system according to claim 6, 2, or 7 wherein said EKG signal providing means includes means for providing three different EKG channel signals indicative of electrical activity associated with a patient's heart action, said sampling means including means for sampling each of the three EKG channel signals provided by the EKG signal providing means, said signal processing means including means for substantially simultaneously analyzing the samples of all three channels provided by said sampling means in real time and according to predetermined criteria.

12. A system according to claim 11 wherein the office unit means comprises means for transmitting to the patient unit via the communication channel patient notification criteria, the memory means of the patient unit including means for storing the patient notification criteria transmitted via the communication channel by the transmitting means of the office unit means, the portable housing means of the patient unit having associated therewith patient notification means, the signal processing means of the patient unit including means for analyzing the EKG samples with respect to the patient notification criteria stored in the associated memory means and causing said patient notification means to be actuated if any of the patient notification criteria are met.

13. A system according to claim 1, 6, 2, 3, 5, 6 or 7 wherein
the sampling means of the patient unit comprises means for digitizing the samples; and
the memory means includes means for storing a plurality of variable length cardiac events, each event comprising a plurality of adjacent EKG digitized values provided by the ditigizing means over a predetermined period of time.

14. A system according to claim 2 or 7, wherein the asymptomatic event recording criteria includes at least one of the following types of criteria: pacemaker failure, ST changes, ectopic runs, tachyarrhythmias, and bradyarrhythmias.

15. A system according to claim 1, 6, 2, 3, 5, 6 or 7 wherein the patient unit further includes means, actuable by the patient, for causing an event to be stored in said memory means.

16. A system according to claim 1, 6, 2, 3, 5, 6 or 7 wherein the signal processing means comprises means for analyzing functional failures of the interaction of a pacemaker with the patient's heart.

17. A system according to claim 1, 6, 2, 3, 5, 6 or 7 wherein the memory means of the patient unit further includes means for storing identification data for identifying the patient and a test being carried out, the identification data being transmitted by said patient actuable transmitting means and being included in the corresponding patient report prepared by the office unit means.

18. A system according to claim 1, 6, 2, 3, 6 or 7 wherein the communication channel is a standard voice-grade telephone channel.

19. A system according to claim 1, 6, 2, 3, 5 or 7 wherein the communication channel is a radio channel.

20. A system according to claim 1, 6, 2, 3, 4, 5 or 7 further including second office unit means, both office unit means having means for communicating with one another via a second communication channel.

21. A system according to claim 1, 6, 2, 3, 4, 5 or 7 wherein the patient unit includes
operating battery means, within the portable housing means thereof, for powering the sampling means, signal processing means and memory means thereof; and
data save battery means within the portable housing means for providing data save power to the memory means when the operating battery means cannot provide sufficient operating power to the sampling means, signal processing means and memory means, the data save battery means providing a sufficient amount of power to preserve data already stored in the memory means.

22. A system according to claim 21 wherein
the patient unit further includes means within the portable housing means for
(a) monitoring a condition of the operating battery means, and
(b) generating battery condition information indicative thereof for storage by the memory means and transmittal by the patient actuable transmitting means.

23. A system according to claim 1, 6, 2, 3, 4, 5 or 7 wherein the portable housing means of the patient unit includes therein means for compressing data to be stored in the memory means before it is stored.

24. A system according to claim 23 wherein the data compressing means comprises means for Huffmann coding the data to be stored in said memory means.

25. A system according to claim 1, 6, 2, 3, 4, 5 or 7 wherein the patient actuatable transmitting means comprises means for transmitting data as a frequency modulated (FM) analog signal.

26. A system according to claim 1, 6, 2, 3, 4, 5 or 7 wherein the patient actuatable transmitting means comprises means for transmitting data as a frequency shift keyed (FSK) digital signal.

27. A system according to claim 1 wherein said office unit means for notifying comprises means for sending a voice synthesized message over a telephone line.

28. A cardiac monitor for an ambulatory patient comprising:
means operatively connectable with a patient's body for providing three EKG channel signals indicative of electrical activity associated with a patient's heart action;
means for sampling each of the three EKG channel signals to provide a plurality of EKG signal samples for each of the three channel signals;
signal processing means for analyzing the EKG signal samples of each of the three channel signals in real time and according to predetermined criteria so as to more easily extract waveforms from a noisy background as a result of analyzation of the EKG samples of each of the three channel signals and generating, as a result of that analysis, processed data including a plurality of cardiac events and statistics related to all heartbeats occurring during a predetermined monitoring period to produce a corresponding patient report intelligible to a person skilled in coronary care;
memory means for storing the processed data generated by the signal processing means;
patient actuable transmitting means for causing the processed data stored in said memory means to be read from said memory means and to be transmitted over a communication channel; and
portable housing means, suitable for being worn or carried by the patient, containing said sampling means, signal processing means, memory means, and transmitting means.

29. A monitor according to claim 28 wherein the memory means includes means for storing asymptomatic event recording criteria transmitted thereto via the communication channel, the signal processing means including means for analyzing the EKG signal samples with respect to the asymptomatic event criteria and causing the event to be stored if any of the criteria are met.

30. A monitor according to claim 28 wherein the memory means includes means for storing patient notification criteria transmitted thereto via the communication channel, the portable housing means having associated therewith patient notification means, the signal processing means including means for analyzing the EKG samples with respect to the patient notification criteria stored in the associated memory means and causing said patient notification means to be acutated if any of the patient notification criteria are met.

31. A monitor according to claim 28 wherein the communication channel is a standard voice-grade telephone channel, said monitor further including telemetry means for transmitting by telemetry the EKG signal provided by the EKG signal providing means to aid in patient hook-up of the monitor.

32. A monitor according to claim 28 wherein the memory means includes means for storing analyzing criteria transmitted thereto via the communication channel, the signal processing means including means for analyzing the EKG signal samples with respect to the analyzing criteria stored in the memory means thereof.

33. A monitor according to claim 32 wherein the memory means includes means for storing asymptomatic event recording criteria transmitted thereto via the communication channel, the signal processing means including means for analyzing the EKG signal samples with respect to the asymptomatic event criteria and causing the event to be stored if any of the criteria are met.

34. A monitor according to claim 32, 29, 31, or 33 wherein the memory means includes means for storing patient notification criteria transmitted thereto via the communication channel, the portable housing means having associated therewith patient notification means, the signal processing means including means for analyzing the EKG samples with respect to the patient notification criteria stored in the associated memory means and causing said patient notification means to be acutated if any of the patient notification criteria are met.

35. A monitor according to claim 32, 29, or 34 wherein the communication channel is a standard voice-grade telephone channel, said patient actuatable transmitting means also including telemetry means for transmitting by telemetry the EKG signal provided by the EKG signal providing means to aid in patient hook-up of the monitor.

36. A monitor according to claim 35 wherein the memory means includes means for storing patient notification criteria transmitted thereto via the communication channel, the portable housing means having associated therewith patient notification means, the signal processing means including means for analyzing the EKG samples with respect to the patient notification criteria stored in the associated memory means and causing said patient notification means to be acutated if any of the patient notification criteria are met.

37. A monitor according to claim 28, 32, 29, 30, 31, or 33 wherein
the sampling means comprises means for digitizing the samples; and
the memory means includes means for storing a plurality of variable length cardiac events, each event comprising a plurality of adjacent EKG digitized values provided by said ditigizing means over a predetermined period of time.

38. A monitor according to claim 29 or 33, wherein the asymptomatic event recording criteria includes at least one of the following types of criteria: pacemaker failure, ST changes, ectopic runs, tachyarrhytmias, and bradyarrhythmias.

39. A monitor according to claim 28, 32, 29, 30, 31, or 33 wherein the portable housing means has associated herewith means, actuable by the patient, for causing an event to be stored in said memory means.

40. A monitor according to claim 28, 32, 29, 30, 31, or 33 wherein the signal processing means comprises means for analyzing functional failures of the interaction of a pacemaker with the patient's heart.

41. A monitor according to claim 28, 32, 29, 30, 31, or 33 wherein the memory means includes means for storing data for identifying the patient and a test being carried out, the identification data being transmitted by said patient actuable transmitting means.

42. A monitor according to claim 28, 32, 29, 30, 31, or 33 wherein the communication channel is a standard voice-grade telephone channel.

43. A monitor according to claim 28, 32, 29, 30, 31, or 33 wherein said portable housing means has mounted therein
operating battery means for powering the sampling means, signal processing means and memory means; and
data save battery means for providing data save power to the memory means when the operating battery means cannot provide sufficient operating power to the sampling means, signal processing means and memory means, the data save battery means providing a sufficient amount of power to preserve data already stored in the memory means.

44. A monitor according to claim 43 wherein
the portable housing means includes means therein for
(a) monitoring a condition of the operating battery means, and
(b) generating battery condition information indicative thereof for storage by the memory means and transmittal by the patient actuable transmitting means.

45. A monitor according to claim 28, 32, 29, 31, 32, or 34 wherein said portable housing means has mounted therein means for compressing data to be stored in the memory means before it is stored.

46. A monitor according to claim 45 wherein the data compressing means comprises means for Huffmann coding the data to be stored in said memory means.

47. A system according to claim 28, 32, 29, 31, 32, or 34 wherein the transmitting means comprises means for transmitting data as a frequency modulated (FM) analog signal.

48. A system according to claim 28, 32, 29, 30, 31, or 33 wherein the transmitting means comprises means for transmitting data as a frequency shift keyed (FSK) digital signal.

49. A cardiac monitor according to claim 28 wherein said analyzing means includes means for analyzing P-waves.

50. A cardiac monitor for an ambulatory patient, comprising:
means operatively connectable with a patient's body for providing three EKG channel signals indicative of electrical activity associated with a patient's heart action;
means for sampling each of the remaining EKG signal channels provided by the EKG signal providing means to provide a plurality of EKG signal samples;
signal processing means for substantially simultaneously analyzing the samples of each of the three EKG channel signals in real time and according to predetermined criteria so as to obtain enhanced waveform analysis by which a waveform is more easily extracted from a noisey background as a result of anlyzation of the EKG sample of each of the three channel signals and generating, as a result of that analysis, processed data including a plurality of cardiac events and statics related to all heartbeats occurring during a predetermined monitoring period to produce a corresponding patient report intelligible to a person skilled in coronary care;

memory means for storing the processed data generated by the signal processing means; and portable housing means, suitable for being worn or carried by the patient, containing said sampling means, signal processing means and memory means.

51. A monitor according to claim 50 wherein the sampling means comprises means for digitizing the samples; and the memory means includes means for storing a plurality of variable length events, each event comprising a plurality of adjacent EKG digitized values provided by said sampling and ditigizing means over a predetermined period of time.

52. A monitor according to claim 51 wherein the portable housing means has associated therewith means, actuable by the patient, for causing an event to be stored in said memory means.

53. A monitor according to claim 51 or 52 wherein each event stored comprises digitized values from a single EKG signal component.

54. A monitor according to claim 51 or 52 wherein each event stored comprises digitized values from two EKG signal components.

55. A monitor according to claim 51 or 52 wherein each event stored comprises digitized values from all three EKG signal components.

56. A monitor according to claim 50, 51 or 52 wherein the signal processing means comprises means for analyzing functional failures of the interaction of a pacemaker with the patient's heart.

57. A monitor according to claim 50, 51 or 52 wherein the memory means includes means for storing identification data for identifying the patient and a test being carried out, the identification data being transmitted by said patient actuable transmitting means.

58. A monitor according to claim 50, 51 or 52 wherein said portable housing means has mounted therein operating battery means for powering the sampling means, signal processing means and memory means; and data save battery means for providing data save power to the memory means when the operating battery means cannot provide sufficient operating power to the sampling means, signal processing means and memory means, the data save battery means providing a sufficient amount of power to preserve data already stored in the memory means.

59. A monitor according to claim 50, 51 or 52 wherein said portable housing means has mounted therein means for compressing data to be stored in the memory means before it is stored.

60. A monitor according to claim 59 wherein the data compressing means comprises means for Huffmann coding the data to be stored in said memory means.

61. A cardiac monitoring system for monitoring an ambulatory patient, comprising:

a cardiac monitoring patient unit for the ambulatory patient comprising:

means operatively connectable with a patient's body for providing an EKG signal indicative of electrical activity associated with a patient's heat action;

means for sampling the EKG signal provided by the EKG signal providing means to provide a plurality of EKG signal samples;

signal processing means for analyzing the EKG signal samples in real time and according to predetermined criteria and generating, as a result of that analysis, processed data including a plurality of cardiac events and statistics related to all heartbeats occurring during a predetermined monitoring period, for inclusion in at least a portion of a corresponding patient report intelligible to a person skilled in coronary care;

memory means for storing the processed data generated by the signal processing means;

portable housing means, suitable for being worn or carried by the patient, containing the sampling means, signal processing means and memory means;

patient actuable transmitting means for causing data including the processed data stored in the memory means to be read from the memory means and to be transmitted over a communication channel; and an office unit means for cooperating with said patient unit, said office unit means having means for automatically and without the necessity of any human operator, receiving the processed data via the communication channel, and means for automatically and without the necessity of any human operator preparing the corresponding patient report.

* * * * *